(12) United States Patent
Zebala et al.

(10) Patent No.: US 9,707,248 B2
(45) Date of Patent: *Jul. 18, 2017

(54) USE OF THIOPYRIMIDINECARBOXAMIDE FOR TREATING CANCER

(71) Applicant: Syntrix Biosystems Inc., Auburn, WA (US)

(72) Inventors: John A. Zebala, Issaquah, WA (US); Dean Y. Maeda, Seattle, WA (US); Aaron D. Schuler, Auburn, WA (US)

(73) Assignee: Syntrix Biosystems Inc., Auburn, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/279,361

(22) Filed: Sep. 28, 2016

(65) Prior Publication Data
US 2017/0014435 A1    Jan. 19, 2017

Related U.S. Application Data

(63) Continuation of application No. 14/610,960, filed on Jan. 30, 2015, which is a continuation of application No. 13/957,665, filed on Aug. 2, 2013, now Pat. No. 8,969,365.

(51) Int. Cl.
| | | |
|---|---|---|
| A61K 45/06 | (2006.01) |
| A61K 31/69 | (2006.01) |
| C07F 5/02 | (2006.01) |
| A61K 9/00 | (2006.01) |

(52) U.S. Cl.
CPC ............ *A61K 31/69* (2013.01); *A61K 9/0053* (2013.01); *A61K 45/06* (2013.01); *C07F 5/025* (2013.01)

(58) Field of Classification Search
CPC ................................ C07F 5/025; A61K 31/69
See application file for complete search history.

(56) References Cited

U.S. PATENT DOCUMENTS

| | | | |
|---|---|---|---|
| 4,139,623 A | 2/1979 | Jaeggi et al. |
| 5,296,506 A | 3/1994 | Kingston et al. |
| 5,405,972 A | 4/1995 | Holton et al. |
| 5,411,984 A | 5/1995 | Kingston et al. |
| 5,422,364 A | 6/1995 | Nicolaou et al. |
| 5,440,057 A | 8/1995 | Nicolaou et al. |
| 5,461,169 A | 10/1995 | Nicolaou et al. |
| 5,468,769 A | 11/1995 | Klein et al. |
| 5,475,120 A | 12/1995 | Rao |
| 5,478,736 A | 12/1995 | Nair |
| 5,478,854 A | 12/1995 | Farina et al. |
| 5,480,884 A | 1/1996 | Thal et al. |
| 5,484,809 A | 1/1996 | Hostetler et al. |
| 5,488,116 A | 1/1996 | Danishefsky et al. |
| 5,489,589 A | 2/1996 | Wittman et al. |
| 5,508,447 A | 4/1996 | Magnus |
| 5,527,924 A | 6/1996 | Danishefsky et al. |
| 5,530,020 A | 6/1996 | Gunawardana et al. |
| 5,565,478 A | 10/1996 | Kohn et al. |
| 5,569,729 A | 10/1996 | Leclerc |
| 5,756,524 A | 5/1998 | Riordan et al. |
| 6,022,884 A | 2/2000 | Mantlo et al. |
| 6,093,723 A | 7/2000 | Miao et al. |
| 6,521,395 B1 | 2/2003 | Begley et al. |
| 6,777,432 B1 | 8/2004 | Cutshall et al. |
| 6,812,226 B2 | 11/2004 | Baxter et al. |
| 7,084,164 B2 | 8/2006 | Tobe et al. |
| 7,176,310 B1 | 2/2007 | Baughman et al. |
| 7,482,355 B2 | 1/2009 | Ebden et al. |
| 7,494,987 B2 | 2/2009 | Akada et al. |
| 7,759,373 B2 | 7/2010 | Hongu et al. |

(Continued)

FOREIGN PATENT DOCUMENTS

| | | |
|---|---|---|
| CN | 1402730 A | 3/2003 |
| JP | H06-505027 A | 6/1994 |

(Continued)

OTHER PUBLICATIONS

U.S. Appl. No. 14/226,672, filed Mar. 26, 2014, Maeda et al.
U.S. Appl. No. 14/283,118, filed May 20, 2014, Maeda et al.
Arenberg et al., "Epithelial-Neutrophil Activating Peptide (ENA-78) is an Important Angiogenic Factor in Non-Small Cell Lung Cancer", J. Clin. Invest., 1998, 102, 465-472.
Arenberg et al., "Inhibition of Interleukin-8 Reduces Tumorigenesis of Human Non-Small Cell Lung Cancer in SCID Mice", J. Clin. Invest., 1996, 97, 2792-2802.
Baggiolini et al., "Interleukin-8, A Chemotactic and Inflammatory Cytokine", Fed. of European Biochemical Societies, 1992, 307(1), 97-101.
Beg et al., "An Essential Role for NF-κB in Preventing TNF-α-Induced Cell Death", Science, 1996, 782-784.
Berge et al., "Pharmaceutical Salts", J. Pharm. Sci., 1977, 66(1), 1-19.
Bulinski et al., "Overexpression of MAP4 Inhibits Organell Motility and Trafficking in Vivo", J. Cell Sci., 1997, 110, 3055-3064.

(Continued)

*Primary Examiner* — Alexander R Pagano
(74) *Attorney, Agent, or Firm* — Baker & Hostetler LLP

(57) ABSTRACT

There is disclosed is a method of treating cancer using compound having formula SX-682

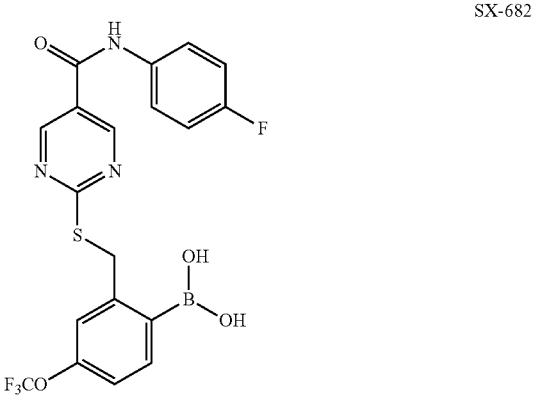

alone or in combination with an antineoplastic agent, microtubule affecting agents, antineoplastic agents, anti-angiogenesis agents, VEGF receptor kinase inhibitors, antibodies against the VEGF receptor, interferon, or radiation.

24 Claims, 5 Drawing Sheets

(56) References Cited

U.S. PATENT DOCUMENTS

| | | | |
|---|---|---|---|
| 8,637,529 B2 | 1/2014 | Woller et al. | |
| 8,748,623 B2* | 6/2014 | Maeda | A61K 31/44 |
| | | | 546/268.4 |
| 8,779,149 B2 | 7/2014 | Maeda et al. | |
| 8,969,365 B2* | 3/2015 | Maeda | C07F 5/025 |
| | | | 514/274 |
| 8,981,106 B2 | 3/2015 | Maeda et al. | |
| 8,993,541 B2 | 3/2015 | Maeda et al. | |
| 2004/0116479 A1 | 6/2004 | Haviv et al. | |
| 2006/0063790 A1 | 3/2006 | Gillman et al. | |
| 2007/0015734 A1 | 1/2007 | McElroy et al. | |
| 2009/0163463 A1 | 6/2009 | Bruce et al. | |
| 2010/0210593 A1* | 8/2010 | Maeda | A61K 31/44 |
| | | | 514/64 |
| 2012/0046243 A1* | 2/2012 | Maeda | A61K 31/44 |
| | | | 514/64 |
| 2014/0206647 A1 | 7/2014 | Maeda et al. | |
| 2014/0256678 A1 | 9/2014 | Maeda et al. | |
| 2015/0038461 A1 | 2/2015 | Zebala et al. | |
| 2015/0147341 A1* | 5/2015 | Zebala | C07F 5/025 |
| | | | 424/158.1 |

FOREIGN PATENT DOCUMENTS

| | | |
|---|---|---|
| JP | 2008-511675 A | 4/2008 |
| JP | 2010-510272 A | 4/2010 |
| JP | 2013-536234 A | 9/2013 |
| WO | WO 93/10102 A1 | 5/1993 |
| WO | WO 01/25242 A1 | 4/2001 |
| WO | WO 02/053544 A1 | 7/2002 |
| WO | WO 03/024448 A2 | 3/2003 |
| WO | WO 2006/028958 A2 | 3/2006 |
| WO | WO 2007/071358 A1 | 6/2007 |
| WO | WO 2008/061795 A2 | 5/2008 |
| WO | WO 2008/073936 A1 | 6/2008 |
| WO | WO 2008/123469 A1 | 10/2008 |
| WO | WO 2008/130320 A2 | 10/2008 |
| WO | WO 2009/016088 A1 | 2/2009 |
| WO | WO 2009/037503 A2 | 3/2009 |
| WO | WO 2009/071476 A1 | 6/2009 |
| WO | WO 2010/007382 A1 | 1/2010 |
| WO | WO 2010/032875 A2 | 3/2010 |
| WO | WO 2010/127978 A1 | 11/2010 |
| WO | WO 2011/025838 A1 | 3/2011 |
| WO | WO 2011/133888 A1 | 10/2011 |
| WO | WO 2012/027289 A1 | 3/2012 |

OTHER PUBLICATIONS

Donnelly et al., "Interleukin-8 and Development of Adult Respiratory Distress Syndrome in At-Risk Patient Groups", Lancet, 1993, 341, 643-647.
Gould, "Salt Selection for Basic Drugs", Intl. J. Pharmaceutics, 1986, 33(1-3), 201-217.
Haghnegandar et al., "The Tumorigenic and Angiogenic Effects of MGSA/GRO Proteins in Melanoma", J. Leukoc. Biology, 2000, 67(1), 53-62.
Inoue et al., "Interleukin 8 Expression Regulates Tumorigenicity and Metastases in Androgen-Independent Prostate Cancer", Clin. Cancer Res., 2000, 6, 2104-2119.
Lopes et al., "Assessment of Microtubule Stabilizers by Semiautomated In Vitro Microtubule Protein Polymerization and Mitotic Block Assays", Cancer Chemotherapy and Pharmacology, Nov. 1997, 41(1), 37-47.
Miller et al., "Biology and Biochemistry of the Chemokines: A Family of Chemotactic and Inflammatory Cytokines", Crit. Rev. Immunol., 1992, 12(2), 17-46.
Miller et al., Elevated Levels of NAP-1/Interleukin-8 are present in the Airspaces of Patients with the Adult Respiratory Distress Syndrome and are Associated with Increased Mortality Am. Rev. Respir. Dis., 1992, 146(2), 427-432.
Muhlradt et al., "Epothilone B Stabilizaes Microtubuli of Macrophages Like Taxol Without Showing Taxol-Like Endotoxin Activity", Cancer Res., 1997, 57,3344-3346.
Nicolaou et al., "Synthesis of Epothilones A and B in Solid and Solution Phase", Nature, 1997, 387, 268-272.
Oppenheim et al., "Properties of the Novel Proinflammatory Supergene 'Intercrine' Cytokine Family", Annu. Rev. Immunol., 1991, 9, 617-648.
Panda et al., "Differential Effects of Vinblastine on Polymerization and Dynamics at Opposite Microtubule Ends", J. Biol. Chem., 1996, 271(47), 29807-29812.
Panda et al., "Stabilization of Microtubule Dynamics by Estramustine by Binding to a Novel Site in Tubulin: A Possible Mechanistic Basis for its Antitumor Action", Proc. Natl. Acad. Sci. USA, 1997, 94,10560-10564.
Seitz et al., "Enhanced Production of Neutrophil-Activating Peptide-1/Interleukin-8 in Rheumatoid Arthritis", J. Clin. Invest., 1991, 87, 463-469.
Service, "Tumor Killer Made; How Does It Work?", Science, 1996, 274, 1 page.
Strieter et al., "The Functional Role of the ELR Motif in CXC Chemokine-mediated Angiogenesis", 1995, 270(45), 27348-27357.
Vasquez et al., "Nanomolar Concentrations of Nocodazole Alter Microtubule Dynamic Instability In Vivo and In Vitro", Mol. Biol. Cell., 1997, 8, 973-985.
Yoneda et. al., "Expression of Angiogenesis-Related Genes and Progression of Human Ovarian Carcinomas in Nude Mice", J. Nat.Cancer Inst., 1998, 90, 447-454.
Yuen et al., "Deprotection of pinacolyl boronate esters via hydrolysis of intermediate potassium trifluoroborates", Tetrahedron Letters, 2005, 46, 7899-7903.
R.L. Auten et al.; 299; The Journal of Pharmacology and Experimental Therapeutics; 90-95; 2001.
R. Bertini et al.; 101 PNAS; 11791-11796; 2004.
C. Bizzari et al.; 112 Pharmacology & Therapeutics; 139-149; 2006.
R.W. Chapman et al.; 121 Pharmacology & Therapeutics; 55-68; 2009.
J.P. Jacobs et al.; 62 Arthritis & Rheumatism; 1921-1932; 2010.
P.L. Podolin et al.; 169 The Journal of Immunology; 6435-6444; 2002.
K. Reich et al.; 116 The Journal of Investigative Dermatology; 319-329; 2001.
Silverman, R.; "The Organic Chemistry of Drug Design and Drug Action," 2004, Elsevier, pp. 29-32.
Cutshall et al.; "Nicotinanilides as Inhibitors of Neutroophil Chemotaxis"; Bioorg. Med. Chem. Letter; 2002, vol. 12, pp. 1517-1520.
Ross; CAPLUS; accession No. 1967:443649; 2013; 1 page.
Winkelmann et al.; CAPLUS; accession No. 1978:443236; 2013; 1 page.
Prachayasittikul et al.; CAPLUS; accession No. 1986:148697; 2013; 1 page.
Sasse et al.; CAPLUS; accession No. 1988:454789; 2013; 5 pages.
Jackman et al.; CAPLUS; accession No. 1988:528959; 2013; 1 page.
Busch-Petersen; "Small Molecule Antagonists of the CXCR2 and CXCR1 Chemokine Receptors as Therapeutic Agents for the Treatment of Inflammatory Diseases" Curr Topics Med Chem. vol. 6 No. 13; 2006; p. 1345-1352.
Nicholls et al.; "Identification of a Putative Intracellular Allosteric Antagonist Binding-Site in the CXC Chemokine Receptors 1 and 2" Mol. Pharm. vol. 74 No. 5; 2008; p. 1193-1202.
Cutshall et al.; "Nicotinamide N-Oxides as CXCR2 Antagonists"; Bioorganic Medicinal Chem. Lett. 11; 2001; p. 1951-1954.
Maeda et al.; "Nicotinamide Glycolates Antagonize CXCR2 Activity through an Intracellular Mechanism"; J. Pharm. Exp. Ther. Vo. 332 No. 1; 2010; p. 145-152.
Thorarensen et al.; CAPLUS; accession No. 2004:182843; 2012; 6 pages.
de Kruijf et al.; "Nonpeptidergic allosteric antagonists differently bind to the CXCR2 chemokine receptor"; J. Pharm. Exp. Ther. vol. 329 No. 2; 2009; p. 783-790.
Cutshall et al.; CAPLUS; accession No. 2002:521710; 2013; 2 pages.
International Patent Application No. PCT/US2013/053376; Int'l Preliminary Report on Patentability; dated Feb. 11, 2016; 7 pages.

(56) References Cited

OTHER PUBLICATIONS

Y.S. Yoon et al.; 9 The International Journal of Tuberculosis and Lung Disease; 2005; p. 1215-1219.
Z. Wang et al.; 19 Drug Delivery Today; 2014; p. 145-150.
U.K. Marelli et al.; 3 Frontiers in Oncology; 2013; p. 1-12.
T.M. Cunha et al.; 154 British Journal of Pharmacology; 2008; p. 460-470.
D.R. Nagarkar et al.; 183 The Journal of Immunology; 2009; p. 6698-6707.
J. Belperio et al.; 110 The Journal of Clinical Investigation; 2002; p. 1703-1716.
R.D. Sue et al.; 172 Journal of Immunology; 2004; p. 3860-3868.

\* cited by examiner

USE OF THIOPYRIMIDINECARBOXAMIDE FOR TREATING CANCER

CROSS REFERENCE TO RELATED APPLICATIONS

This application is a continuation of U.S. patent application Ser. No. 14/610,960 filed on Jan. 30, 2015, which is a continuation of U.S. patent application Ser. No. 13/957,665, filed Aug. 2, 2013, now U.S. Pat. No. 8,969,365, issued Mar. 3, 2015, the entire contents of which are herein incorporated by reference.

GOVERNMENT RIGHTS

This invention was made with government support under Grant No. HL072614 awarded by the National Institutes of Health. The government has certain rights in the invention.

TECHNICAL FIELD

The present disclosure provides a method of treating cancer using a pyridinecarboxamide or pyrimidinecarboxamide compound, and pharmaceutical compositions for inhalation that include these compounds.

BACKGROUND

Chemokines are chemotactic proteins that have the potential to attract macrophages, T-cells, eosinophils, basophils, neutrophils and endothelial cells to sites of inflammation and tumor growth. Chemokines are typically low molecular mass (7-9 kD) proteins that can be divided into four subfamilies: CC (or β-chemokines), CXC, C (or γ-chemokines) and CX3C (or δ-chemokines). The chemokines are categorized through their primary amino acid structure. The CXC subfamily is characterized by two conserved Cys residues (C) near the N-terminus and separated by an amino acid (X). The CXC-chemokines include, for example, interleukin-8 (IL-8), neutrophil-activating protein-1 (NAP-1), neutrophil-activating protein-2 (NAP-2), GROα, GROβ, GROγ, ENA-78, GCP-2, IP-10, MIG and PF4. The CXC subfamily of chemokines is further characterized by the presence or absence of a specific amino acid sequence, glutamic acid-leucine-arginine (or ELR for short) immediately before the first Cys residue of the CXC motif. Those chemokines with the ELR motif (ELRCXC) are important for the recruitment and activation of neutrophils to sites of inflammation. GROα and IL-8 are examples of ELRCXC chemokines.

The CXC-chemokines mediate their chemotactic activity through interaction with the chemokine receptors CXCR1 and CXCR2. CXCR1 binds IL-8 and GCP-2 with high affinity while CXCR2 binds all ELRCXC chemokines with high affinity.

Since CXC-chemokines promote the accumulation and activation of neutrophils, CXC-chemokines have been implicated in a wide range of acute and chronic inflammatory disorders including COPD, psoriasis and rheumatoid arthritis. (Baggiolini, 1992, *FEBS Lett*, 307:97; Miller, 1992. *Crit Rev Immunol*. 12:17; Oppenheim, 1991, *Annu Rev Immunol*, 9:617; Seitz, 1991, *J Clin Invest*, 87:463; Miller, 1992, *Am Rev Respir Dis*, 146:427; Donnely, 1998, *Lancet*, 341:643).

ELRCXC chemokines, including IL-8, GROα, GROβ, GROγ, NAP-2, and ENA-78 (Strieter, 1995, *J Biol Chem*, 270:27348-57), have also been implicated in the induction of tumor angiogenesis (new blood vessel growth). Angiogenic activity is due to ELRCXC-chemokine binding to, and activation of CXCR2, and possibly CXCR1 for IL-8, expressed on the surface of vascular endothelial cells (ECs) in surrounding vessels.

Many different types of tumors have been shown to produce ELRCXC chemokines. Chemokine production has been correlated with a more aggressive phenotype (Inoue, 2000, *Clin Cancer Res*, 6:2104-2119) and poor prognosis (Yoneda, 1998, *J Nat Cancer Inst*, 90:447-54). Chemokines are potent chemotactic factors and the ELRCXC chemokines, in particular, have been shown to induce EC chemotaxis. Thus, these chemokines are thought to induce chemotaxis of endothelial cells toward their site of production in the tumor. This may be a critical step in the induction of angiogenesis by the tumor. Inhibitors of CXCR2 or dual inhibitors of CXCR2 and CXCR1 will inhibit the angiogenic activity of the ELRCXC chemokines and therefore block the growth of the tumor. This anti-tumor activity has been demonstrated for antibodies to IL-8 (Arenberg, 1996, *J Clin Invest*, 97:2792-802), ENA-78 (Arenberg, 1998, *J Clin Invest*, 102:465-72), and GROα (Haghnegandar, 2000, *J Leukoc Biology*, 67:53-62).

Therefore, there is a need in the art to find CXCR1/2 inhibitor compounds and modulator compounds that can be used as pharmaceutical compounds. There remains a need for compounds that are capable of modulating activity at CXC-chemokine receptors. For example, conditions associated with an increase in IL-8 production (which is responsible for chemotaxis of neutrophil and T-cell subsets into the inflammatory site and growth of tumors) would benefit by compounds that are inhibitors of IL-8 receptor binding. The present disclosure was made to satisfy this need.

SUMMARY

The present disclosure further provides the compound having the formula SX-682

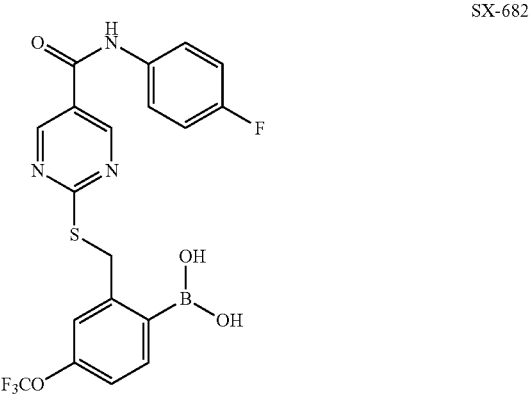 [SMILES: O=C(Nc1ccc(F)cc1)c1cnc(SCc2cc(OC(F)(F)F)ccc2B(O)O)nc1]

The present disclosure further provides a pharmaceutical composition comprising the compound having the formula SX-682, or a pharmaceutically acceptable salt, or solvate thereof and a pharmaceutically acceptable carrier. In certain embodiments, this disclosure provides SX-682 as a novel compound that is a CXC chemokine-modulator, pharmaceutical compositions comprising SX-682, and methods of treatment, prevention, inhibition, or amelioration of one or more diseases associated with CXC chemokine mediation using SX-682 and compositions disclosed herein.

The present disclosure provides a method for treating a disease or disorder selected from the group consisting of pain (e.g., acute pain, acute inflammatory pain, chronic inflammatory pain, and neuropathic pain), acute inflammation, chronic inflammation, rheumatoid arthritis, psoriasis, atopic dermatitis, asthma, bronchopulmonary dysplasia, COPD, adult respiratory disease, arthritis, inflammatory bowel disease, Crohn's disease, ulcerative colitis, septic shock, endotoxic shock, gram negative sepsis, toxic shock syndrome, stroke, ischemia reperfusion injury, renal reperfusion injury, glomerulonephritis, thrombosis, Alzheimer's disease, graft vs. host reaction (i.e., graft-versus-host disease), allograft rejections (e.g., acute allograft rejection, and chronic allograft rejection), malaria, acute respiratory distress syndrome, delayed type hypersensitivity reaction, atherosclerosis, cerebral ischemia, cardiac ischemia, osteoarthritis, multiple sclerosis, restinosis, angiogenesis, angiogenesis associated with tumor growth, osteoporosis, gingivitis, respiratory viruses, herpes viruses, hepatitis viruses, HIV, Kaposi's sarcoma associated virus (i.e., Kaposi's sarcoma), meningitis, cystic fibrosis, pre-term labor, cough, pruritis, multi-organ dysfunction, trauma, strains, sprains, contusions, psoriatic arthritis, herpes, encephalitis, CNS vasculitis, traumatic brain injury, systemic tumors, CNS tumors, tumors dependent on angiogenesis for growth, leukopenia and neutropenia, chemotherapy-induced leukopenia and neutropenia, opportunistic infections associated with neutropenia or leukopenia, subarachnoid hemorrhage, post-surgical trauma, interstitial pneumonitis, hypersensitivity, crystal induced arthritis, acute pancreatitis, chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred, corneal neovascularization, polymyositis, vasculitis, acne, gastric ulcers, duodenal ulcers, celiac disease, esophagitis, glossitis, airflow obstruction, airway hyperresponsiveness (i.e., airway hyperreactivity), bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy (i.e., the treatment of burns), periodontitis, cancer, transplant reperfusion injury, and early transplantation rejection (e.g., acute allograft rejection) in a patient in need of such treatment, comprising administering an effective amount of the compound having the formula SX-682.

DETAILED DESCRIPTION OF ILLUSTRATIVE EMBODIMENTS

Definitions

Figure 1:
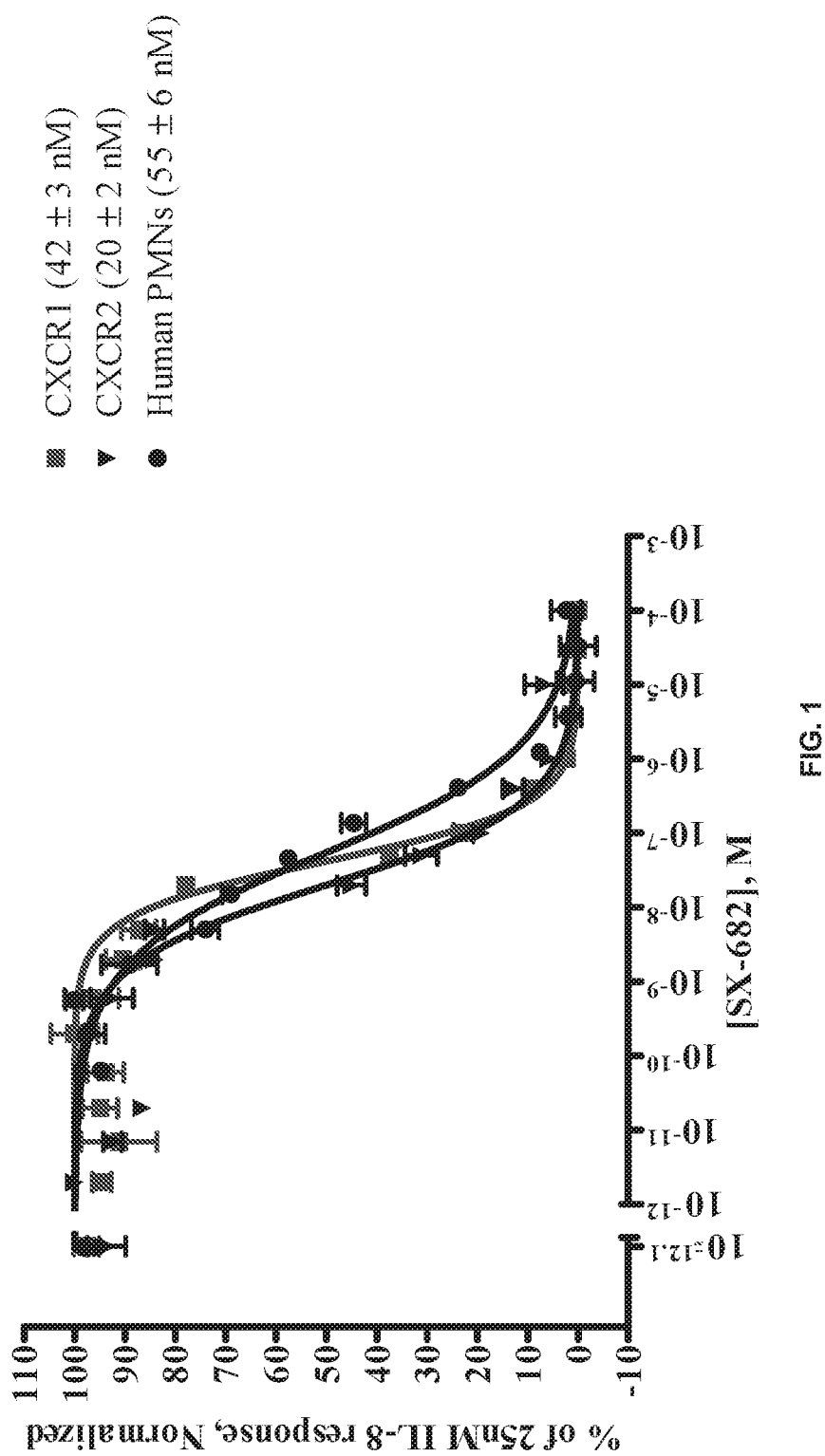
FIG. 1 illustrates SX-682 inhibition of CXCL8-mediated intracellular calcium flux in isolated human neutrophils ('Human PMNs'), RBL cells stably transfected with CXCR1 (legend 'CXCR1'), and RBL cells stably transfected with CXCR2 (legend 'CXCR2'). Mean (n=4, ±SE) $IC_{50}$ values for SX-682 in each cell system are in parentheses in the legend.

When any substituent or variable occurs more than one time in any moiety, its definition on each occurrence is independent of its definition at every other occurrence. Also, combinations of substituents and/or variables are permissible only if such combinations result in stable compounds.

Unless indicated otherwise, the following definitions apply throughout the present specification and claims. These definitions apply regardless of whether a term is used by itself or in combination with other terms. For example, the definition of "alkyl" also applies to the "alkyl" portion of the defined term "alkoxy".

"An effective amount" or a "therapeutically effective amount" means to describe an amount of compound of the present disclosure or another agent effective to treat a mammal (e.g., a human) having a disease or CXC chemokine-mediated condition, and thus producing the desired therapeutic effect.

"At least one" means one or more (e.g., 1-3, 1-2, or 1).

"Composition" includes a product comprising the specified ingredients in the specified amounts, as well as any product that results, directly or indirectly, from combination of the specified ingredients in the specified amounts.

"In combination with" as used to describe the administration of SX-682 with other medicaments in the methods of treatment of this invention, means—that SX-682 and the other medicaments are administered sequentially or concurrently in separate dosage forms, or are administered concurrently in the same dosage form.

"Mammal" means a human or other mammal, or means a human being.

"Patient" includes both human and other mammals, preferably human.

"Prodrug" denotes a compound that is a drug precursor which, upon administration to a subject, undergoes chemical conversion by metabolic or chemical processes to yield SX-682 or a salt and/or solvate thereof. A discussion of pro-drugs is provided in Higuchi, *Pro-drugs as Novel Delivery Systems*, v. 14 of the A.C.S. Symp Series, and in Bioreversible Carriers in Drug Design, Roche, ed., Am Pharma Assoc, Pergamon Press, 1987, both of which are incorporated herein by reference.

"Alkyl" is a saturated or unsaturated, straight or branched, hydrocarbon chain. In various embodiments, the alkyl group has 1-18 carbon atoms, i.e. is a $C_1$-$C_{18}$ group, or is a $C_1$-$C_{12}$ group, a $C_1$-$C_6$ group, or a $C_1$-$C_4$ group. A lower alkyl group has 1-6 carbons. Independently, in various embodiments, the alkyl group has zero branches (i.e., is a straight chain), one branch, two branches, or more than two branches. Independently, in one embodiment, the alkyl group is saturated. In another embodiment, the alkyl group is unsaturated. In various embodiments, the unsaturated alkyl may have one double bond, two double bonds, more than two double bonds, and/or one triple bond, two triple bonds, or more than two triple bonds. Alkyl chains may be optionally substituted with 1 substituent (i.e., the alkyl group is mono-substituted), or 1-2 substituents, or 1-3 substituents, or 1-4 substituents, etc. The substituents may be selected from the group consisting of hydroxy, amino, alkylamino, boronyl, carboxy, nitro, cyano, and the like. When the alkyl group incorporates one or more heteroatoms, the alkyl group is referred to herein as a heteroalkyl group. When the substituents on an alkyl group are hydrocarbons, then the resulting group is simply referred to as a substituted alkyl. In various aspects, the alkyl group including substituents has less than 25, 24, 23, 22, 21, 20, 19, 18, 17, 16, 15, 14, 13, 12, 11, 10, 9, 8, or 7 carbons.

"Lower alkyl" means a group having about 1 to about 6 carbon atoms in the chain which chain may be straight or branched. Non-limiting examples of suitable alkyl groups include methyl, ethyl, n-propyl, isopropyl, n-butyl, t-butyl, n-pentyl, heptyl, nonyl, and decyl.

"Alkoxy" means an alkyl-O-group wherein alkyl is as defined above. Non-limiting examples of alkoxy groups include: methoxy, ethoxy, n-propoxy, isopropoxy, n-butoxy and heptoxy. The bond to the parent moiety is through the ether oxygen.

"Alkoxyalkyl" means an alkoxy-alkyl-group in which the alkoxy and alkyl are as previously described. Preferred alkoxyalkyl comprise a lower alkyl group. The bond to the parent moiety is through the alkyl.

"Alkylaryl" means an alkyl-aryl-group in which the alkyl and aryl are as previously described. Preferred alkylaryls comprise a lower alkyl group. The bond to the parent moiety is through the aryl.

"Aminoalkyl" means an $NH_2$-alkyl-group, wherein alkyl is as defined above, bound to the parent moiety through the alkyl group.

"Aryl" (sometimes abbreviated "Ar") is an aromatic carbocyclic hydrocarbon ring system. The ring system may be monocyclic or fused polycyclic (e.g., bicyclic, tricyclic, etc.). In one embodiment, the aryl group is monocyclic, and is preferably a $C_6$ ring system, i.e. a phenyl ring is a preferred aryl ring, where preferred bicyclic aryl rings are $C_8$-$C_{12}$, or $C_9$-$C_{10}$. A naphthyl ring, which has 10 carbon atoms, is a preferred polycyclic aryl ring. Unless otherwise indicated herein, the term "aryl" as used herein is meant to include aryl rings optionally substituted by one or more substituents selected from acyl (—C(O)—R), alkoxy (—O—R), alkyl, aryl, alkylamino (—N(H)—R and —N(R)R), alkylthio (—S—R), amino (—$NH_2$), azido (—$N_3$), boronyl (—B(R)R or —B(OH)$_2$ or —B(OR)$_2$), carboxy (—C(O)—OH), alkoxycarbonyl (—C(O)—OR), aminocarbonyl (—C(O)—$NH_2$), aminosulfonyl (—S(O)$_2$—$NH_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—$CH_mX_n$, where m+n=3, X=F, Cl, Br), mercapto (—SH and —S—R) and nitro (—$NO_2$) where each R group is an alkyl group having less than about 12 carbons, preferably where the R group is a lower alkyl group. Non-limiting examples of suitable aryl groups include: phenyl, naphthyl, indenyl, tetrahydronaphthyl, indanyl, anthracenyl, and fluorenyl.

"Arylalkyl" refers to an alkyl group as defined substituted by one or more aryl groups as defined below. Phenyl and naphthyl are preferred aryl groups in an arylalkyl group. A preferred alkyl group is methyl, so that a preferred arylalkyl group is benzyl or benzyl having one or more substituents on the phenyl ring. Unless otherwise indicated, the term "arylalkyl" as used herein is meant to include arylalkyl groups wherein the aryl ring therein is optionally substituted by one or more substituents selected from acyl (—C(O)—R), alkoxy (—O—R), alkyl, aryl, alkylamino (—N(H)—R and —N(R)R), alkylthio (—S—R), amino (—$NH_2$), azido (—$N_3$), boronyl (—B(R)R or —B(OH)$_2$ or —B(OR)$_2$), carboxy (—C(O)—OH), alkoxycarbonyl (—C(O)—OR), aminocarbonyl (—C(O)—$NH_2$), aminosulfonyl (—S(O)$_2$—$NH_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—$CH_mX_n$, where m+n=3, X=F, Cl, Br), mercapto (—SH and —S—R) and nitro (—$NO_2$) where each R is an alkyl group having less than about 12 carbons, preferably where the R group is a lower alkyl group.

"Arylalkyl" means an aryl-alkyl-group in which the aryl and alkyl are as previously described. Preferred arylalkyls comprise a lower alkyl group. Non-limiting examples of suitable aralkyl groups include benzyl, 2-phenethyl and napthalenylmethyl. The bond to the parent moiety is through the alkyl.

"Aryloxy" means an aryl-O-group in which the aryl group is as previously described. Non-limiting examples of suitable aryloxy groups include phenoxy and naphthoxy. The bond to the parent moiety is through the ether oxygen.

"Carboxyalkyl" means an HOOC-alkyl-group, wherein alkyl is as defined above, bound to the parent moiety through the alkyl group.

"Chemokine" means a protein molecule involved in chemotaxis.

A "chemokine-mediated disease" means a disease of which at least one element or cause is related to the regulation of a CXC chemokine.

"Commercially available chemicals" and the chemicals used in the Examples set forth herein may be obtained from standard commercial sources, where such sources include, for example, Acros Organics (Pittsburgh, Pa.), Sigma-Aldrich Chemical (Milwaukee, Wis.), Avocado Research (Lancashire, U.K.), Bionet (Cornwall, U.K.), Boron Molecular (Research Triangle Park, N.C.), Combi-Blocks (San Diego, Calif.), Eastman Organic Chemicals, Eastman Kodak Company (Rochester, N.Y.), Fisher Scientific Co. (Pittsburgh, Pa.), Frontier Scientific (Logan, Utah), ICN Biomedicals, Inc. (Costa Mesa, Calif.), Lancaster Synthesis (Windham, N.H.), Maybridge Chemical Co. (Cornwall, U.K.), Pierce Chemical Co. (Rockford, Ill.), Riedel de Haen (Hannover, Germany), Spectrum Quality Product, Inc. (New Brunswick, N.J.), TCI America (Portland, Oreg.), and Wako Chemicals USA, Inc. (Richmond, Va.).

"Compounds described in the chemical literature" may be identified through reference books and databases directed to chemical compounds and chemical reactions, as known to one of ordinary skill in the art. Suitable reference books and treatise that detail the synthesis of reactants useful in the preparation of compounds disclosed herein, or provide references to articles that describe the preparation of compounds disclosed herein, include for example, "Synthetic Organic Chemistry", John Wiley and Sons, Inc. New York; S. R. Sandler et al, "Organic Functional Group Preparations," $2^{nd}$ Ed., Academic Press, New York, 1983; H. O. House, "Modern Synthetic Reactions," $2^{nd}$ Ed., W. A. Benjamin, Inc. Menlo Park, Calif., 1972; T. L. Glichrist, "Heterocyclic Chemistry," $2^{nd}$ Ed. John Wiley and Sons, New York, 1992; J. March, "Advanced Organic Chemistry: reactions, Mechanisms and Structure," 5$^{th}$ Ed., Wiley Interscience, New York, 2001; Specific and analogous reactants may also be identified through the indices of known chemicals prepared by the Chemical Abstract Service of the American Chemical Society, which are available in most public and university libraries, as well as through online databases (the American Chemical Society, Washington, D.C.). Chemicals that are known but not commercially available in catalogs may be prepared by custom chemical synthesis houses, where many of the standard chemical supply houses (e.g. those listed above) provide custom synthesis services.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. A multicyclic cycloalkyl substituent may include fused, Spiro, or bridged ring structures. Non-limiting examples of suitable monocyclic cycloalkyls include cyclopropyl, cyclobutyl, cyclopentyl, cyclohexyl, cycloheptyl and the like. Non-limiting examples of suitable multicyclic cycloalkyls include 1-decalin, norbornyl, adamantly and the like. Cycloalkyl substituents may be substituted or unsubstituted. In one embodiment, the cycloalkyl is unsubstituted. In another embodiment, the cycloalkyl is substituted with, e.g., 1 substituent (i.e., the cycloalkyl group is mono-substituted), or 1-2 substituents, or 1-3 substituents, or 1-4 substituents, etc. In one embodiment, the substituents that may be present on the cycloalkyl aliphatic ring are selected from acyl (—C(O)—R), alkoxy (—O—R), alkyl, aryl, alkylamino (—N(H)—R and —N(R)R), alkylthio (—S—R), amino (—NH$_2$), azido (—N$_3$), boronyl (—B(R)R or —B(OH)$_2$ or —B(OR)$_2$), carboxy (—C(O)—OH), alkoxycarbonyl (—C(O)—OR), aminocarbonyl (—C(O)—NH$_2$), aminosulfonyl (—S(O)$_2$—NH$_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—CH$_m$X$_n$, where m+n=3, X=F, Cl, Br), mercapto (—SH and —S—R) and nitro (—NO$_2$). In one aspect the R group in the above substituents is an alkyl group having less than about 12 carbons, while in another aspect the R group is a lower alkyl group.

"Cycloalkylalkyl" means a cycloalkyl group bound to the parent moiety through an alkyl group. Non-limiting examples include: cyclopropylmethyl and cyclohexylmethyl.

"Cycloalkylaryl" means a cycloalkyl group bound to the parent moiety through an aryl group. Non-limiting examples include: cyclopropylphenyl and cyclohexylphenyl.

"Effective amount" or "therapeutically effective amount" is meant to describe an amount of compound or a composition of the present disclosure effective in decreasing or increasing (i.e., modulating) the action of a CXC chemokine at a CXC chemokine receptor and thus producing the desired therapeutic effect in a suitable patient.

"Fluoroalkoxy" means an alkoxy group as defined above wherein one or more hydrogen atoms on the alkoxy is or are replaced by a fluoro group.

"Fluoroalkyl" means an alkyl group as defined above wherein one or more hydrogen atoms on the alkyl are replaced by a fluoro group.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine and bromine.

"Heteroalkyl" is a saturated or unsaturated, straight or branched, chain containing carbon and at least one heteroatom. The heteroalkyl group may, in various embodiments, have on heteroatom, or 1-2 heteroatoms, or 1-3 heteroatoms, or 1-4 heteroatoms. In one aspect the heteroalkyl chain contains from 1 to 18 (i.e., 1-18) member atoms (carbon and heteroatoms), and in various embodiments contain 1-12, or 1-6, or 1-4 member atoms. Independently, in various embodiments, the heteroalkyl group has zero branches (i.e., is a straight chain), one branch, two branches, or more than two branches. Independently, in one embodiment, the heteroalkyl group is saturated. In another embodiment, the heteroalkyl group is unsaturated. In various embodiments, the unsaturated heteroalkyl may have one double bond, two double bonds, more than two double bonds, and/or one triple bond, two triple bonds, or more than two triple bonds. Heteroalkyl chains may be substituted or unsubstituted. In one embodiment, the heteroalkyl chain is unsubstituted. In another embodiment, the heteroalkyl chain is substituted. A substituted heteroalkyl chain may have 1 substituent (i.e., by monosubstituted), or may have 1-2 substituents, or 1-3 substituents, or 1-4 substituents, etc. Exemplary heteroalkyl substituents include esters (—C(O)—O—R) and carbonyls (—C(O)—).

"Heterocyclic" (or "heterocycloalkyl" or "heterocyclyl") refers to a non-aromatic saturated monocyclic or multicyclic ring system comprising 3 to 10 ring atoms (e.g., 3 to 7 ring atoms), or 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Examples of heterocyclics or heterocycloalkyls include rings having 5 to 6 ring atoms. The prefix aza, oxa or thia before the heterocyclic or heterocycloalkyl root name means that at least a nitrogen, oxygen or sulfur atom, respectively, is present as a ring atom. The nitrogen or sulfur atom of the heterocyclic or heterocycloalkyl can be optionally oxidized to the corresponding N-oxide, S-oxide or S,S-dioxide. Any nitrogen atoms may be optionally quaternized. Non-limiting examples of monocyclic heterocyclic or heterocycloalkyl rings include: piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophen-yl, and tetrahydrothiopyranyl The heterocyclyl may be unsubstituted or substituted. In one embodiment, the heterocyclyl is unsubstituted. In another embodiment, the heterocyclyl is substituted. The substituted heterocyclyl ring may contain 1 substituent, or 1-2 substituents, or 1-3 substituents, or 1-4 substituents, etc. In one embodiment, the substituents that may be present on the heterocyclyl ring are selected from acyl (—C(O)—R), alkoxy (—O—R), alkyl, aryl, alkylamino (—N(H)—R and —N(R)R), alkylthio (—S—R), amino (—NH$_2$), azido (—N$_3$), boronyl (—B(R)R or —B(OH)$_2$ or —B(OR)$_2$), carboxy (—C(O)—OH), alkoxycarbonyl (—C(O)—OR), aminocarbonyl (—C(O)—NH$_2$), aminosulfonyl (—S(O)$_2$—NH$_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—CH$_m$X$_n$, where m+n=3, X=F, Cl, Br), mercapto (—SH and —S—R) and nitro (—NO$_2$). In one aspect, the R group which is, or is part of the substituent attached to the heterocyclic ring is an alkyl group having less than about 12 carbons, while in another aspect the R group is a lower alkyl group.

"Heterocycloalkylalkyl" means a heterocycloalkyl-alkyl group, wherein said heterocycloalkyl and said alkyl are as defined above, bound to a parent moiety through the alkyl group.

"Heteroaryl" means an aromatic monocyclic or multicyclic ring system comprising 5 to 14 ring atoms, or 5 to 10 ring atoms, in which one or more of the ring atoms is an element other than carbon, for example nitrogen, oxygen or sulfur, alone or in combination. Heteroaryls can contain 5 to 6 ring atoms. The prefix aza, oxa or thio before the heteroaryl root name means that at least a nitrogen, oxygen or sulfur atom respectively, is present as a ring atom. A nitrogen atom of a heteroaryl can be optionally oxidized to the corresponding N-oxide. Any nitrogen atoms may be optionally quaternized. Non-limiting examples of heteroaryls include: pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl. The heteroaryl may be unsubstituted or substituted. In one embodiment, the heteroaryl is unsubstituted. In another embodiment, the heteroaryl is substituted. The substituted heteroaryl ring may contain 1 substituent, or 1-2 substituents, or 1-3 substituents, or 1-4 substituents, etc. In one embodiment, the substituents that may be present on the heteroaryl ring are selected from acyl (—C(O)—R), alkoxy (—O—R), alkyl, aryl, alkylamino (—N(H)—R and —N(R)R), alkylthio (—S—R), amino (—NH$_2$), azido (—N$_3$), boronyl (—B(R)R or —B(OH)$_2$ or —B(OR)$_2$), carboxy (—C(O)—OH), alkoxycarbonyl (—C(O)—OR), aminocarbonyl (—C(O)—NH$_2$), aminosulfonyl (—S(O)$_2$—NH$_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—CH$_m$X$_n$, where m+n=3, X=F, Cl, Br), mercapto (—SH and —S—R) and nitro (—NO$_2$). In one aspect, the R group which is, or is part of the substituent attached to the heteroaryl ring is an alkyl group having less than about 12 carbons, while in another aspect the R group is a lower alkyl group.

"Heteroarylkyl" or "heteroarylalkyl" means a heteroarylalkyl-group, in which the heteroaryl and alkyl are as previously described. Preferred heteroaralkyls can contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Hydroxyalkyl" means an HO-alkyl-group, in which alkyl is previously defined. Preferred hydroxyalkyls contain lower alkyl. Non-limiting examples of suitable hydroxyalkyl groups include hydroxymethyl and 2-hydroxyethyl.

"Hydrate" is a solvate wherein the solvent molecule is H$_2$O.

"Solvate" means a physical association of a compound of this disclosure with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

Examples of "disease modifying antirheumatic drugs" (i.e., DMARDs) include, for example, methotrexate, aminopterin, sulfasalzine, leflunomide, TNFa directed agents (e.g., infliximab, etanercept, and adalimumab), IL-1 directed agents (e.g., anakinra) B cell directed agents (e.g., rituximab), T cell directed agents (e.g., alefacept, efalizumab, and CTLA4-Ig), TNFa-converting enzyme inhibitors, interleukin-1 converting enzyme is inhibitors, and p38 kinase inhibitors.

The term "other classes of compounds indicated for the treatment of rheumatoid arthritis", as used herein, unless indicated otherwise, means: compounds selected from the group consisting of: IL-1 directed agents (e.g., anakinra); B cell directed agents (e.g., rituximab); T cell directed agents (e.g., alefacept, efalizumab, and CTLA4-Ig), TNFa-converting enzyme inhibitors, interleukin-1 converting enzyme inhibitors, and p38 kinase inhibitors.

The compound having the formula SX-682 forms salts that are also within the scope of this disclosure. Reference to the compound having the formula SX-682 herein is understood to include reference to salts thereof, unless otherwise indicated. The term "salt(s)", as employed herein, denotes acidic salts formed with inorganic and/or organic acids, as well as basic salts formed with inorganic and/or organic bases. The salts can be pharmaceutically acceptable (i.e., non-toxic, physiologically acceptable) salts, although other salts are also useful. Salts of the compound having the formula SX-682 may be formed, for example, by reacting it with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemi sulfates, heptanoates, hexanoates, hydrochlorides, hydrobromides, hydroiodides, 2-hydroxyethanesulfonates, lactates, maleates, methanesulfonates, 2-napthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like. Additionally, acids which are generally considered suitable for the formation of pharmaceutically useful salts from basic pharmaceutical compounds are discussed, for example, by Berge, 1977, *J. Pharma Sci*, 66:1-19; Gould, 1986, *Int'l J Pharmaceutics*, 33:201-17; Anderson, The Practice of Medicinal Chemistry (1996), Acad Press, New York; and in The Orange Book (Food & Drug Administration, Washington, D.C.). These disclosures are incorporated herein by reference herein.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl, and stearyl chlorides, bromides and iodides), arylalkyl halides (e.g., benzyl and phenethyl bromides), and others.

All such acid and base salts are intended to be pharmaceutically acceptable salts within the scope of the disclosure and all acid and base salts are considered equivalent to the free forms of the corresponding compounds for purposes of the disclosure.

The compound having the formula SX-682 can exist in unsolvated and solvated forms, including hydrated forms. In general, the solvated forms, with pharmaceutically acceptable solvents such as water, ethanol and the like, are equivalent to the unsolvated forms for the purposes of this disclosure.

The compound having the formula SX-682 and salts, solvates and prodrugs thereof, may exist in their tautomeric form (for example, as an amide or imino ether). All such tautomeric forms are contemplated herein as part of the present disclosure.

Also within the scope of the present disclosure are polymorphs of the compounds of this disclosure (i.e., polymorphs of the compound having the formula SX-682 are within the scope of this disclosure).

Prodrugs of the compound having the formula SX-682 or pharmaceutically acceptable salts or solvates thereof are within the scope of this disclosure.

All stereoisomers (for example, geometric isomers, optical isomers and the like) of the compound having the formula SX-682 (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure. Individual stereoisomers of the compounds of this disclosure may, for example, be substantially free of other isomers, or may be admixed, for example, as racemates or with all other, or other selected, stereoisomers. The chiral centers of the compounds herein can have the S or R configuration as defined by the IUPAC 1974 Recommendations. The use of the terms "salt", "solvate", "prodrug" and the like, is intended to equally apply to the salt, solvate and prodrug of enantiomers, stereoisomers, rotamers, tautomers, racemates or prodrugs of the disclosed compounds.

Classes of compounds that can be used as the chemotherapeutic agent (antineoplastic agent) include: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): uracil mustard, chlormethine, cyclophosphamide, ifosfamide, m elphalan, chlorambucil, pipobroman, triethylene-melamine, t riethylenethiophos-phoramine, busulfan, carmustine, lomustine, streptozocin, dacarbazine, and temozolomide.

Antimetabolites (including folic acid antagonists, pyrimidine analogs, purine analogs and adenosine deaminase inhibitors): methotrexate, aminopterin, 5-fluorouracil, floxuridine, cytarabine, 6-mercaptopurine, 6-thioguanine, fludarabine phosphate, pentostatine, and gemcitabine.

Natural products and their derivatives (including vinca alkaloids, antitumor antibiotics, enzymes, lymphokines and epipodophyllotoxins): vinblastine, vincristine, vindesine, bleomycin, dactinomycin, daunorubicin, doxorubicin, epirubicin, idarubicin, paclitaxel (TAXOL®), mithramycin, deoxycoformycin, mitomycin-C, L-asparaginase, interferons (especially IFN-γ), etoposide, and teniposide.

Hormones and steroids (including synthetic analogs): 17α-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, zoladex.

Synthetics (including inorganic complexes such as platinum coordination complexes): cisplatin, carboplatin, hydroxyurea, amsacrine, procarbazine, mitotane, mitoxantrone, levamisole, and hexamethylmelamine.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 2008 edition (Thomson P D R, Montvale, N.J. 07645); the disclosure of which is incorporated herein by reference herein.

As used herein, a microtubule affecting agent is a compound that interferes with cellular mitosis, i.e., having an anti-mitotic effect, by affecting microtubule formation and/or action. Such agents can be, for instance, microtubule stabilizing agents or agents that disrupt microtubule formation.

Microtubule affecting agents useful in this disclosure are well known to those of skilled in the art and include, but are not limited to allocolchicine (NSC 406042), halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (TAXOL®, NSC 125973), TAXOL® derivatives (e.g., derivatives (e.g., NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, 1996, *Science*, 274:2009) estramustine, nocodazole, MAP4, and the like. Examples of such agents are also described in the scientific and patent literature, see, e.g., Bulinski, 1997, *J Cell Sci*, 110:3055-64; Panda, 1997, *Proc Natl Acad Sci USA*, 94:10560-64; Muhlradt, 1997, *Cancer Res*, 57:3344-46; Nicolaou, 1997, *Nature*, 387:268-72; Vasquez, 1997, *Mol Biol Cell*, 8:973-85; and Panda, 1996, *J Biol Chem*, 271:29807-12.

Particularly, agents can be compounds with paclitaxel-like activity. These include, but are not limited to paclitaxel and paclitaxel derivatives (paclitaxel-like compounds) and analogues. Paclitaxel and its derivatives are available commercially. In addition, methods of making paclitaxel and paclitaxel derivatives and analogues are well known to those of skilled in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506, the disclosures of which are incorporated by reference herein).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes, 1997, *Cancer Chemother Pharmacol,* 41:37-47).

Therapeutic Activity

Modulators of neutrophil activity can have great therapeutic benefit in a number of indications. In disease states characterized by an improperly heightened neutrophil response, an inhibitor of neutrophil activity would be indicated. In patients suffering from, for example neutropenia, a neutrophil agonist or activator has clinical benefit. In vivo evaluation of two lead compounds SX-517 and SX-576 in the murine air-pouch model of inflammation, revealed that both inhibitory and agonist activity on neutrophils were achieved, depending on the dose given.

Methods of Treatment

One embodiment is directed to a pharmaceutical composition comprising SX-682 or a pharmaceutically acceptable salt or solvate thereof, in combination with a pharmaceutically acceptable carrier.

The methods of treatment of this disclosure are advantageous in treating diseases where the ELR-CXC chemokine binds to CXCR2. Another embodiment of the disclosure is directed to a method of treating CXCR1/2 chemokine mediated diseases in a patient in need of such treatment comprising administering to the patient a therapeutically effective amount of compound SX-682, or a pharmaceutically acceptable salt or solvate thereof.

Another embodiment of the disclosure is a method of treating CXCR1/2 chemokine mediated diseases in a patient in need thereof comprising administering to the patient (a) an effective amount of the compound having the formula SX-682, or a pharmaceutically acceptable salt or solvate thereof, concurrently or sequentially with (b) at least one additional agent, drug, medicament, antibody and/or inhibitor useful for the treatment of CXCR1/2 chemokine mediated diseases. Examples of the additional medicament, drug or agent include, but are not limited to, disease modifying antirheumatic drugs; nonsteroidal antiinflammatory drugs (NSAIDs); COX-2 selective inhibitors; COX-1 inhibitors; immunosuppressives; steroids; biological response modifiers; and other anti-inflammatory agents or therapeutics useful for the treatment of CXCR1/2 chemokine mediated diseases.

Another embodiment of the method of treating a CXCR1/2 chemokine mediated disease is administering (a) a therapeutically effective amount of the compound having the formula SX-682, or a pharmaceutically acceptable salt or solvate thereof, concurrently or sequentially with (b) at least one medicament selected from the group consisting of: disease modifying antirheumatic drugs; nonsteroidal antiinflammatory drugs; COX-2 selective inhibitors; COX-1 inhibitors; immunosuppressives; steroids; biological response modifiers; and other anti-inflammatory agents or therapeutics useful for the treatment of CXCR1 and/or CXCR2 chemokine mediated diseases.

Another embodiment of this disclosure is a method for treating cancer in a patient in need of such treatment, the method comprises administering to said patient a therapeutically effective amount of the compound having the formula SX-682, or a pharmaceutically acceptable salt or solvate thereof. Another embodiment of this disclosure is a method for treating cancer comprising administering to the patient a therapeutic amount of the compound having the formula SX-682, or a pharmaceutically acceptable salt or solvate thereof, concurrently or sequentially with (a) at least one antineoplastic agent selected from the group consisting of: (1) gemcitabine, (2) paclitaxel, (3) 5-fluorouracil (5-FU), (4) cyclo-phosphamide, (5) temozolomide and (6) vincristine or (b) at least one agent selected from the group consisting of (1) microtubule affecting agents, (2) antineoplastic agents, (3) anti-angiogenesis agents, (4) VEGF receptor kinase inhibitors, (5) antibodies against the VEGF receptor, (6) interferon, and (7) radiation.

Another embodiment of this disclosure is a method for treating asthma in a patient in need of such treatment the method comprising administering to the patient a therapeutically effective amount of the compound having the formula SX-682, or a pharmaceutically acceptable salt or solvate thereof. Another embodiment of this disclosure is a method for treating a pulmonary disease (e.g., COPD, asthma, or cystic fibrosis), in a patient in need of such treatment, the method comprising administering to the patient a therapeutically effective amount of: (a) the compound having the formula SX-682, or a pharmaceutically acceptable salt or solvate thereof, concurrently or sequentially with (b) at least one compound selected from the group consisting of: glucocorticoids, 5-lipoxygenase inhibitors, beta-2 adrenoceptor agonists, muscarinic M1 antagonists, muscarinic M3 antagonists, muscarinic M2 agonists, NK3 antagonists, LTB4 antagonists, cysteinyl leukotriene antagonists, bronchodilators, PDE4 inhibitors, PDE inhibitors, elastase inhibitors, MMP inhibitors, phospholipase A2 inhibitors, phospholipase D inhibitors, histamine H1 antagonists, histamine H3 antagonists, dopamine agonists, adenosine A2 agonists, NK1 and NK2 antagonists, GABA-$\beta$ agonists, nociceptin agonists, expectorants, mucolytic agents, decongestants, antioxidants, anti-IL-8 antibodies, anti-IL-5 antibodies, anti-IgE antibodies, anti-TNF antibodies, IL-10, adhesion molecule inhibitors, and growth hormones.

Another embodiment of this disclosure is a method for treating multiple sclerosis, comprising administering to the patient: (a) a therapeutically effective amount of the compound having the formula SX-682, or a pharmaceutically acceptable salt or solvate thereof, concurrently or sequentially with (b) a therapeutically effective amount of at least one compound selected from the group consisting of: glatiramer acetate, glucocorticoids, methotrexate, azothioprine, mitoxantrone, and CB2-selective inhibitors.

Another embodiment of this disclosure is a method of treating multiple sclerosis comprising concurrent or sequential administration of a therapeutically effective amount of: (a) the compound having the formula SX-682, or a pharmaceutically acceptable salt or solvate thereof, and (b) at least one compound selected from the group consisting of: methotrexate, cyclosporin, leflunimide, sulfasalazine, $\beta$-methasone, $\beta$-interferon, glatiramer acetate, prednisone, etonercept, and infliximab.

Another embodiment of this disclosure is a method for treating rheumatoid arthritis in a patient in need of such treatment comprising administering to said patient a therapeutically effective amount of the compound having the formula SX-682, or a pharmaceutically acceptable salt or solvate thereof.

Another embodiment of this disclosure is a method for treating rheumatoid arthritis in a patient in need of such treatment comprising administering to said patient a therapeutically effective amount of the compound having the formula SX-682, or a pharmaceutically acceptable salt or solvate thereof, in combination with at least one compound selected from the group consisting of COX-2 inhibitors, COX-1 inhibitors, immunosuppressives (e.g., methotrexate, aminopterin, cyclosporin, leflunimide and sulfasalazine), steroids (e.g., betamethasone, cortisone and dexamethasone), PDE 4 inhibitors, anti-TNF-alpha compounds, MMP inhibitors, glucocorticoids, chemokine inhibitors, CB2-selective agents, and other classes of compounds indicated for the treatment of rheumatoid arthritis.

Another embodiment of this disclosure is a method for treating stroke and ischemia reperfusion injury in a patient in need of such treatment the method comprising administering to the patient a therapeutically effective amount of: (a) the compound having the formula SX-682, or a pharmaceutically acceptable salt or solvate thereof, concurrently or sequentially with (b) at least one compound selected from the group consisting of: thrombolitics (e.g., tenecteplase, TPA, alteplase), antiplatelet agents (e.g., gpIIb/IIIa), antagonists (e.g., abciximab and eftiifbatide), anticoagulants (e.g., heparin), and other compounds indicated for the treatment of stroke and ischemia reperfusion injury.

Another embodiment of this disclosure is a method for treating stroke and ischemia reperfusion injury in a patient in need of such treatment the method comprising administering to the patient a therapeutically effective amount of: (a) the compound having the formula SX-682, or a pharmaceutically acceptable salt or solvate thereof concurrently or sequentially with (b) at least one compound selected from the group consisting of: tenecteplase, TPA, alteplase, abciximab, eftiifbatide, and heparin.

Another embodiment of this disclosure is a method for treating psoriasis in a patient in need of such treatment, the method comprising administering to the patient a therapeutically effective amount of: a) the compound having the formula SX-682, or a pharmaceutically acceptable salt or solvate thereof, concurrently or sequentially with (b) at least one compound selected from the group consisting of: immunosuppressives (e.g., methotrexate, aminopterin, cyclosporin, efalizumab, alefacept, leflunimide and sulfasalazine), steroids (e.g., β-methasone) and anti-TNFα compounds (e.g., etonercept and infliximab).

This disclosure also provides a method for treating CXCR1/2 mediated disease or condition selected from the group consisting of: pain (e.g., acute pain, acute inflammatory pain, chronic inflammatory pain, and neuropathic pain), acute inflammation, chronic inflammation, rheumatoid arthritis, psoriasis, atopic dermatitis, asthma, bronchopulmonary dysplasia, COPD, adult respiratory disease, arthritis, inflammatory bowel disease, Crohn's disease, ulcerative colitis, septic shock, endotoxic shock, gram negative sepsis, toxic shock syndrome, stroke, ischemia reperfusion injury, renal reperfusion injury, glomerulonephritis, thrombosis, Alzheimer's disease, graft vs. host reaction (i.e., graft-versus-host disease), allograft rejections (e.g., acute allograft rejection, and chronic allograft rejection), malaria, acute respiratory distress syndrome, delayed type hypersensitivity reaction, atherosclerosis, cerebral ischemia, cardiac ischemia, osteoarthritis, multiple sclerosis, restinosis, angiogenesis, associated with tumor growth, osteoporosis, gingivitis, respiratory viruses, herpes viruses, hepatitis viruses, HIV, Kaposi's sarcoma associated virus (i.e., Kaposi's sarcoma), meningitis, cystic fibrosis, pre-term labor, cough, pruritis, multi-organ dysfunction, trauma, strains, sprains, contusions, psoriatic arthritis, herpes, encephalitis, CNS vasculitis, traumatic brain injury, systemic tumors, CNS tumors, tumors dependent on angiogenesis for growth, leukopenia and neutropenia, chemotherapy-induced leukopenia and neutropenia, opportunistic infections associated with neutropenia or leukopenia, subarachnoid hemorrhage, post surgical trauma, interstitial pneumonitis, hypersensitivity, crystal induced arthritis, acute pancreatitis, chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred, corneal neovascularization, polymyositis, vasculitis, acne, gastric ulcers, duodenal ulcers, celiac disease, esophagitis, glossitis, airflow obstruction, airway hyperresponsiveness (i.e., airway hyperreactivity), bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy (i.e., the treatment of burns), periodontitis, cancer, transplant reperfusion injury, early transplantation rejection (e.g., acute allograft rejection) in a patient in need of such treatment comprising administering to said patient an effective amount of the compound having the formula SX-682, or a pharmaceutically acceptable salt or solvate thereof.

Another embodiment of this disclosure is a method for treating diseases such as allograft rejections, early transplantation rejections, autoimmune deafness, myocarditis, neuropathies, autoimmune diseases and vasculitis syndromes wherein said:

(a) allograft rejections are selected from the group consisting of acute allograft rejections and chronic allograft rejections;

(b) early transplantation rejection is an acute allograft rejection; (c) autoimmune deafness is Meniere's disease;

(d) myocarditis is viral myocarditis;

(e) neuropathies are selected from the group consisting of IgA neuropathy, membranous neuropathy and idiopathic neuropathy;

(f) autoimmune diseases are anemias; and (g) vasculitis syndromes are selected from the group consisting of giant cell arteries, Behcet's disease and Wegener's granulomatosis.

Another embodiment of this disclosure is a method for treating COPD in a patient in need of such treatment comprising administering to said patient a therapeutically effective amount of the compound having the formula SX-682, or a pharmaceutically acceptable salt or solvate thereof.

Another embodiment of this disclosure is a method for treating arthritis in a patient in need of such treatment comprising administering to said patient a therapeutically effective amount of the compound having the formula SX-682, or a pharmaceutically acceptable salt or solvate thereof.

Another embodiment of this disclosure is a method for treating osteoarthritis in a patient in need of such treatment comprising administering to said patient a therapeutically effective amount of the compound having the formula SX-682, or a pharmaceutically acceptable salt or solvate thereof.

Another embodiment of this disclosure is a method for treating pain in a patient in need of such treatment comprising administering to said patient a therapeutically effective amount of the compound having the formula SX-682, or a pharmaceutically acceptable salt or solvate thereof.

Another embodiment of this disclosure is a method for treating pain in a patient in need of such treatment comprising administering to said patient a therapeutically effective amount of the compound having the formula SX-682, or a pharmaceutically acceptable salt or solvate thereof, and administering a therapeutically effective amount of at least one medicament selected from the group consisting of: NSAIDs, COMB inhibitors (e.g., COX-1 and COX-2 inhibitors), anti-depressants, and anti-convulsants.

Another embodiment of this disclosure is a method for treating acute pain in a patient in need of such treatment comprising administering to said patient a therapeutically effective amount of the compound having the formula SX-682, or a pharmaceutically acceptable salt or solvate thereof.

Another embodiment of this disclosure is a method for treating acute inflammatory pain in a patient in need of such treatment comprising administering to said patient a therapeutically effective amount of the compound having the formula SX-682, or a pharmaceutically acceptable salt or solvate thereof.

Another embodiment of this disclosure is a method for treating chronic inflammatory pain in a patient in need of such treatment comprising administering to said-patient a therapeutically effective amount of the compound having the formula SX-682, or a pharmaceutically acceptable salt or solvate thereof.

Another embodiment of this disclosure is a method for treating neuropathic pain in a patient in need of such treatment comprising administering to said patient a therapeutically effective amount of the compound having the formula SX-682, or a pharmaceutically acceptable salt or solvate thereof.

Another embodiment of this disclosure is a pharmaceutical composition comprising the compound having the formula SX-682, or a pharmaceutically acceptable salt or solvate thereof, and at least one other agent, medicament, antibody and/or inhibitor disclosed above, and a pharmaceutically acceptable carrier.

In general the compounds used to treat pain will have CXCR1/2 antagonistic activity.

NSAIDs are well known to those skilled in the art and can be used in their known dosages and dosage regimens. Examples of NSAIDs include but are not limited to: piroxicam, ketoprofen, naproxen, indomethacin, and ibuprofen COXIB inhibitors are well known to those skilled in the art and can be used in their known dosages and dosage regimens. Examples of COXIB inhibitors include, but are not limited to: rofecoxib and celecoxib. Anti-depressants are well known to those skilled in the art and can be used in their known dosages and dosage regimens. Examples of anti-depressants include but are not limited to: amitriptyline and nortriptyline. Anti-convulsants are well known to those skilled in the art and can be used in their known dosages and dosage regimens. Examples of anti-convulsants include but are not limited to: gabapentin, carbamazepine, pregabalin, and lamotragine.

Pharmaceutical Compositions

For preparing pharmaceutical compositions from the compound of formula SX-682, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, microcrystalline cellulose, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington: The Science and Practice of Pharmacy,* 20th Edition, (2000), Lippincott Williams & Wilkins, Baltimore, Md. which is incorporated herein by reference.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration. Liquid form preparations may also include dissolution in lipid-based, self-emulsifying drug delivery systems (SEDDS) such as LABRASOL® or GELUCIRE® for oral administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compound of formula SX-682 may also be deliverable transdermally. The transdermal composition can take the form of creams, lotions, aerosols and/or emulsions and can be included in a transdermal patch of the matrix or reservoir type as are conventional in the art for this purpose.

The compound of formula SX-682 can be administered orally.

A suitable pharmaceutical preparation is in a unit dosage form. In such form, the preparation is subdivided into suitably sized unit doses containing appropriate quantities of the active component, e.g., an effective amount to achieve the desired purpose.

The quantity of active compound of formula SX-682 in a unit dose of preparation may be varied or adjusted from about 0.01 mg to about 1000 mg, or from about 0.01 mg to about 750 mg, or from about 0.01 mg to about 500 mg, or from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

The amount and frequency of administration of the compound of formula SX-682 and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses, or given preferably as a single once-daily dose. Once-weekly and twice-weekly dosing is also preferable.

The amount and frequency of administration of the compound of formula SX-682 and the chemotherapeutic agents and/or radiation therapy will be regulated according to the judgment of the attending clinician (physician) considering such factors as age, condition and size of the patient as well as severity of the disease being treated. A dosage regimen of the compound having the formula SX-682 can be orally administration of from 10 mg to 2000 mg/day, or 10 to 1000 mg/day, or 50 to 600 mg/day, in two to four (or two) divided doses, to block tumor growth. Intermittent therapy (e.g., one week out of three weeks or three out of four weeks) may also be used.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

If the compound of formula SX-682, and the chemotherapeutic agent and/or radiation is not administered simultaneously or essentially simultaneously, then the initial order of administration of the compound of formula SX-682, and the chemotherapeutic agent and/or radiation, may not be important. Thus, the compound of formula SX-682 may be administered first, followed by the administration of the chemotherapeutic agent and/or radiation; or the chemotherapeutic agent and/or radiation may be administered first, followed by the administration of the compound of formula SX-682. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient.

For example, the chemotherapeutic agent and/or radiation may be administered first, especially if it is a cytotoxic agent, and then the treatment continued with the administration of the compound having the formula SX-682 followed, where determined advantageous, by the administration of the chemotherapeutic agent and/or radiation, and so on until the treatment protocol is complete.

The particular choice of the compound of formula SX-682, and chemotherapeutic agent and/or radiation will depend upon the diagnosis of the attending physicians and their judgment of the condition of the patient and the appropriate treatment protocol.

Also, in general, the compound of formula SX-682 and the chemotherapeutic agent do not have to be administered in the same pharmaceutical composition, and may, because of different physical and chemical characteristics, have to be administered by different routes. For example, the compound of formula SX-682 may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

Thus, in accordance with experience and knowledge, the practicing physician can modify each protocol for the administration of a component (therapeutic agent; i.e., the compound of formula SX-682, chemotherapeutic agent or radiation) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MM scan, and successive measurements can be used to judge whether or not growth of the tumor has been retarded or even reversed. Relief of disease-related symptoms such as pain, and improvement in overall condition can also be used to help judge effectiveness of treatment.

The disclosure provided herein is exemplified by the following preparations and examples that should not be construed to limit the scope of the disclosure. Alternative mechanistic pathways and analogous structures may be apparent to those skilled in the art.

Synthesis Example 1

Synthesis of
N-(4-fluorophenyl)-2-chloro-pyrimidinamide 3

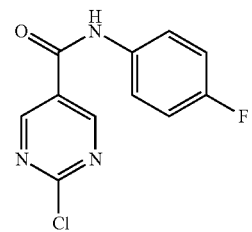 [SMILES: O=C(Nc1ccc(F)cc1)c1cnc(Cl)nc1]

2-Chloro-pyrimidine-5-carboxylic acid (3.16 g, 20 mmol) was suspended in dichloromethane (40 mL), and oxalyl chloride (3.30 g, 26 mmol) was added, followed by dimethylformamide as catalyst. The reaction started to vigorously evolve gas. The reaction was heated to reflux for 1 hour, then allowed to cool to room temperature. 4-Fluoroaniline was added, vigorous bubbling was seen again, and the reaction mixture warmed up considerably. Triethylamine was added, and a flocculent precipitate immediately formed. The reaction mixture was heated to reflux once again for another hour, removed from heat, and stirred at room temperature for 18 hours under nitrogen. The reaction was diluted with ethyl acetate (100 mL), and the organic layer washed with water, saturated sodium bicarbonate, water, 11\T HCl, water, saturated sodium chloride, then dried over sodium sulfate. The liquid was filtered, and evaporated to yield 3.44 g (68%) of compound 3 as a light yellow solid. ESI-MS m/z=252.0 [M+H]$^+$.

Synthesis Example 2

Synthesis of 2-Mercapto-pyrimidine-5-carboxylic acid (4-fluoro-phenyl)-amide Intermediate 4

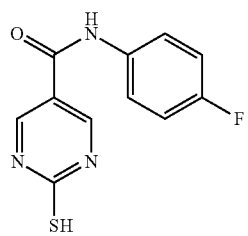 [SMILES: O=C(Nc1ccc(F)cc1)c1cnc(S)nc1]

In a round bottom flask, 2-chloro-pyrimidine-5-carboxylic acid (4-fluoro-phenyl)-amide 3 (2.52 g, 10.0 mmol) and anhydrous sodium hydrogen sulfide (1.22 g, 21.8 mmol) were suspended in anhydrous dimethylformamide (20 mL). The suspension was stirred at room temperature, and the reaction mixture turned a deep green color. After 1 h, the reaction mixture was partoned between ethyl acetate and water, and transferred to a separatory funnel. After the layers were separated, the ethyl acetate layer was washed twice with a 2:1 mixture of water and 5% sodium bicarbonate. The combined aqueous layers were acidified with 1 N HCl precipitating a yellow solid. The suspension was left to stand at room temperature for 2 hours, then the precipitate was collected by vacuum filtration, rinsing with water. The yellow solid was dried overnight in a vacuum desiccator to yield 2.3 g (92%) of the thiopyrimidinamide intermediate 4. ESI-MS m/z=250.0 [M+H]$^+$. $^1$H NMR (300 MHz, DMSO-d$_6$) δ 10.29 (s, 1H), 8.77 (bs, 2H), 7.77-7.70 (m, 2H), 7.24 (t, J=8.9 Hz, 2H).

Synthesis Example 3

Synthesis of Pinacol Ester Derivative 5

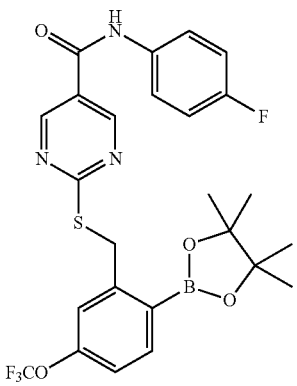 [SMILES: CC1(C)OB(c2ccc(OC(F)(F)F)cc2CSc2ncc(C(=O)Nc3ccc(F)cc3)cn2)OC1(C)C]

2-Mercapto-pyrimidine-5-carboxylic acid (4-fluoro-phenyl)-amide intermediate 4 (2.32 g, 9.3 mmol) and 2-bromomethyl-4-trifluoromethoxy-phenylboronic acid, pinacol ester (3.85 g, 10.1 mmol) were suspended in anhydrous DMF (20 ml). Sonication was used to dissolve the compounds. To the reaction flask triethylamine (2.8 mL, 20.1 mmol) was added and a precipitate (triethylamine-HBr) formed immediately. The reaction was layered with nitrogen gas and left to stand at room temperature for 3.75 hr. The reaction was poured into water (500 mL) and layered with ethyl acetate. The biphasic solution was transferred to a separatory funnel and diluted further with ethyl acetate and brine. The layers were separated, and the aqueous layer was extracted twice more with ethyl acetate. The combined ethyl acetate layers were dried over sodium sulfate, gravity filtered, and dried in vacu to yield 5.7 g (>100%, 93% pure by LC-MS) of a red oil, 2-[2-(4,4,5,5-Tetramethyl-[1,3,2]dioxaborolan-2-yl)-5-trifluoromethoxy-benzylsulfanyl]-pyrimidine-5-carboxylic acid (4-fluoro-phenyl)-amide 6. ESI-MS m/z=550.1 [M+H]$^+$. $^1$H NMR (500 MHz, DMSO-d$_6$) δ 10.52 (s, 1H), 9.11 (s, 2H), 7.81 (d, J=8.2 Hz, 1H), 7.78-7.75 (m, 2H), 7.55 (s, 1H), 7.28-7.22 (m, 3H), 4.72 (s, 2H), 1.32 (s, 12H). The NMR spectrum also contained peaks consistent with the presence of residual DMF. The product was carried forward without further purification.

Synthesis Example 4

Synthesis of Compound SX-682

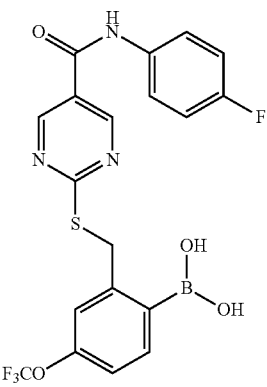 [SMILES: O=C(Nc1ccc(F)cc1)c1cnc(SCc2cc(OC(F)(F)F)ccc2B(O)O)nc1]

SX-682 was obtained by deprotection of the boronic acid pinacol ester. Compound 6 (5.66 g, 10.3 mmol, 1 eq.) was dissolved in methanol (100 mL). The reaction vessel was charged with 4.5 M aqueous potassium hydrogen fluoride (11.5 mL, 5 eq.) and the resulting orange solution was stirred for 1 hour. The methanol was removed by rotary evaporation at room temperature and the resulting mixture of yellow and off-white solids was suspended in acetone. The suspension was gravity filtered to remove the insoluble salts, and the resulting clear yellow solution was added via pipette to a flask of water (2 L) and placed in the refrigerator. After cooling for about 1.5 hours, the resulting off-white precipitate was collected by vacuum filtration, rinsing with water. The funnel was dried overnight in a vacuum desiccator to afford 3.87 g (80% yield, >99% purity by LC-MS) of 2-(2-boronic acid-5-trifluoromethoxy-benzylsulfanyl)-pyrimidine-5-carboxylic acid (4-fluoro-phenyl)-amide. ESI-MS m/z=468.1 [M+H]$^+$. $^1$H NMR (300 MHz, DMSO-d6) δ 10.49 (s, 1H), 9.09 (s, 2H), 8.33 (bs, 2H), 7.78-7.73 (m, 2H), 7.66 (d, J=8.5 Hz, 1H), 7.46 (s, 1H), 7.25-7.19 (m, 3H), 4.70 (s, 2H).

Pharmacology Example 1

In Vitro Inhibition of Intracellular Calcium Release by SX-682

An in vitro assay showed inhibition of CXCR1/2-mediated intracellular calcium release by SX-682. Briefly, cells (either isolated human neutrophils or RBL cells stably transfected with either CXCR1 or CXCR2) were suspended in HBSS$^-$ (without $Ca^{2+}$ and $Mg^{2+}$) containing 10 mM HEPES and FLIPR calcium 3 dye ($3.1 \times 10^7$ cells in total volume 1.7 mL). Cells were aliquoted (200 µL of the cell suspension per tube, 8 tubes total) and 2 µL of the designated compound (with appropriate dilutions) were added to each of 6 tubes. As controls, 2 µL of DMSO (1% final concentration) were added to 2 other tubes. Cells were incubated for 30 min at 37° C. After dye loading, tubes were centrifuged at 6,000 rpm for 1 min, supernatant was removed and the cell pellet was re-suspended in 200 µL of HBSS$^+$ (with $Ca^{2+}$ and $Mg^{2+}$) containing 10 mM HEPES. The test compound or DMSO (control) was added again at the same concentrations that were used during cell loading. The cell suspension was aliquoted into a 96-well reading plate (Corning) in a volume of 90 µL ($10^5$ cells/well). The compound plate contained agonist (CXCL8 in HBSS$^-$) or HBSS$^-$ (control). After 15 sec of reading the basal level of fluorescence by FlexStation II, 10 µL of CXCL8 or HBSS$^-$ were automatically transferred from the compound plate into the reading plate (final concentration of CXCL8 was 25 nM). Changes in fluorescence were monitored (ex=485 nm, em=525 nm) every 5 s for 240 to 500 s at room temperature.

The maximum change in fluorescence, expressed in arbitrary units over baseline (Max–Min), was used to determine the CXCL8 response. The effect of each compound on the CXCL8 response was normalized and expressed as a percent of the DMSO control, which was designated as "100% response." Curve fitting and calculation of the compound inhibitory concentration that reduces the level of the CXCL8 response by 50% ($IC_{50}$), or the compound agonist concentration that increases the level of the calcium release by 50% of the maximum agonist-induced change ($EC_{50}$) were determined by nonlinear regression analysis of the dose-response curves generated using Prism 4 (GraphPad Software, Inc., San Diego, Calif.).

The mean (±SE) $IC_{50}$ for SX-682 (n=4) was 42±3 nM, 20±2 nM and 55±6 nM in CXCR1 transfected RBL cells ('CXCR1', squares), CXCR2 transfected RBL cells ('CXCR2', inverted triangles), and human neutrophils ('Human PMNs', circles), respectively (FIG. 1).

Pharmacology Example 2

SX-682 Exhibits Sustained Wash-Resistant Inhibition of Intracellular Calcium Release SX-682 contains a boronic acid moiety that has the potential to form a transient covalent linkage with hydroxyl-bearing amino acid side chains in the binding site of its protein target. Without wishing to be bound by theory, we hypothesized that such a transient covalent linkage in the binding site of SX-682 might result in CXCR1/2 inhibition that was sustained after inhibitor washout. If inhibition is sustained in vitro after SX-682 washout, inhibition may also be sustained in vivo after SX-682 has been eliminated from the plasma, a property that would permit infrequent patient dosing regimens (e.g. once-daily, twice-weekly and once-weekly). Infrequent dosing regimens are preferred embodiments.

In order to test this hypothesis, RBL cells ($10^7$ cells/mL) stably transfected with either CXCR1 or CXCR2 were (1) incubated with SX-682 at various concentrations for 30 minutes at 37° C., (2) washed and resuspended in assay buffer (RPMI/2% serum) at room temperature, and (3) assayed for CXCL8-mediated calcium response at time points up to 12 h after inhibitor washout. The concentrations of SX-682 tested were 0 (positive control), 0 (negative control), 0.4, 2, and 10 µM. At 30 minutes before each time point, a 56.25 µL aliquot of the cells were removed and loaded for 30 minutes at room temperature in the dark with FLIPR-3 reagent (262.5 µL per tube). Following FLIPR-3 incubation, cells were assayed for CXCL8 mediated intracellular calcium release as described in Pharmacology Example 1.

Figure 2:
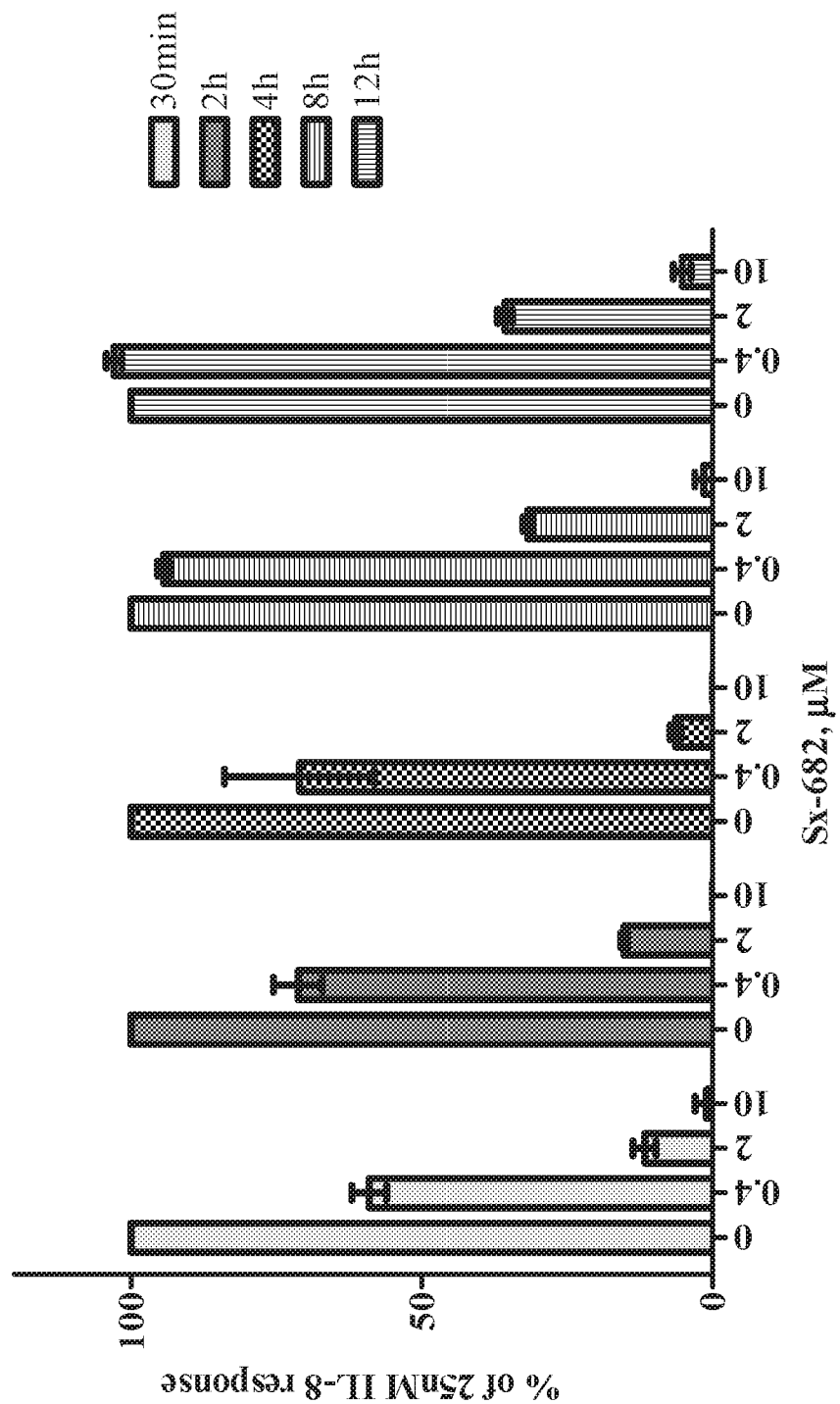
FIG. 2 illustrates that inhibition of CXCL8-mediated intracellular calcium flux in RBL cells stably transfected with CXCR1 is sustained for at least 12 hours after SX-682 washout.
Figure 3:
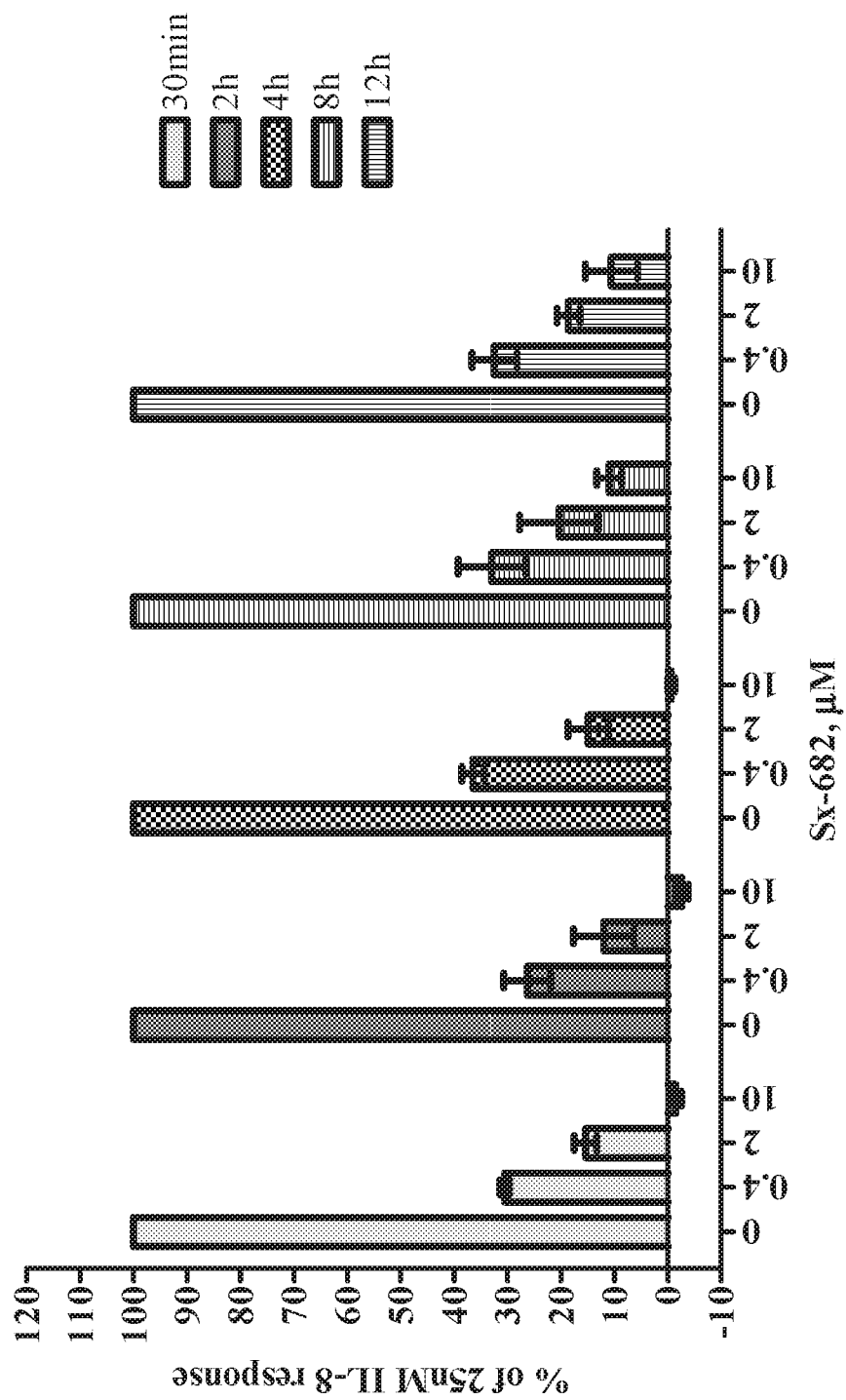
FIG. 3 illustrates that inhibition of CXCL8-mediated intracellular calcium flux in RBL cells stably transfected with CXCR2 is sustained for at least 12 hours after SX-682 washout.

Consistent with our hypothesis, SX-628 exhibited inhibition of CXCL8-mediated intracellular calcium flux in RBL cells stably transfected with either CXCR1 (FIG. 2) or CXCR2 (FIG. 3) that was sustained for at least 12 hours after SX-682 washout.

Pharmacology Example 3

SX-682 Exhibits Pronounced Activity in the Rat Model of Pulmonary Inflammation

Figure 4:
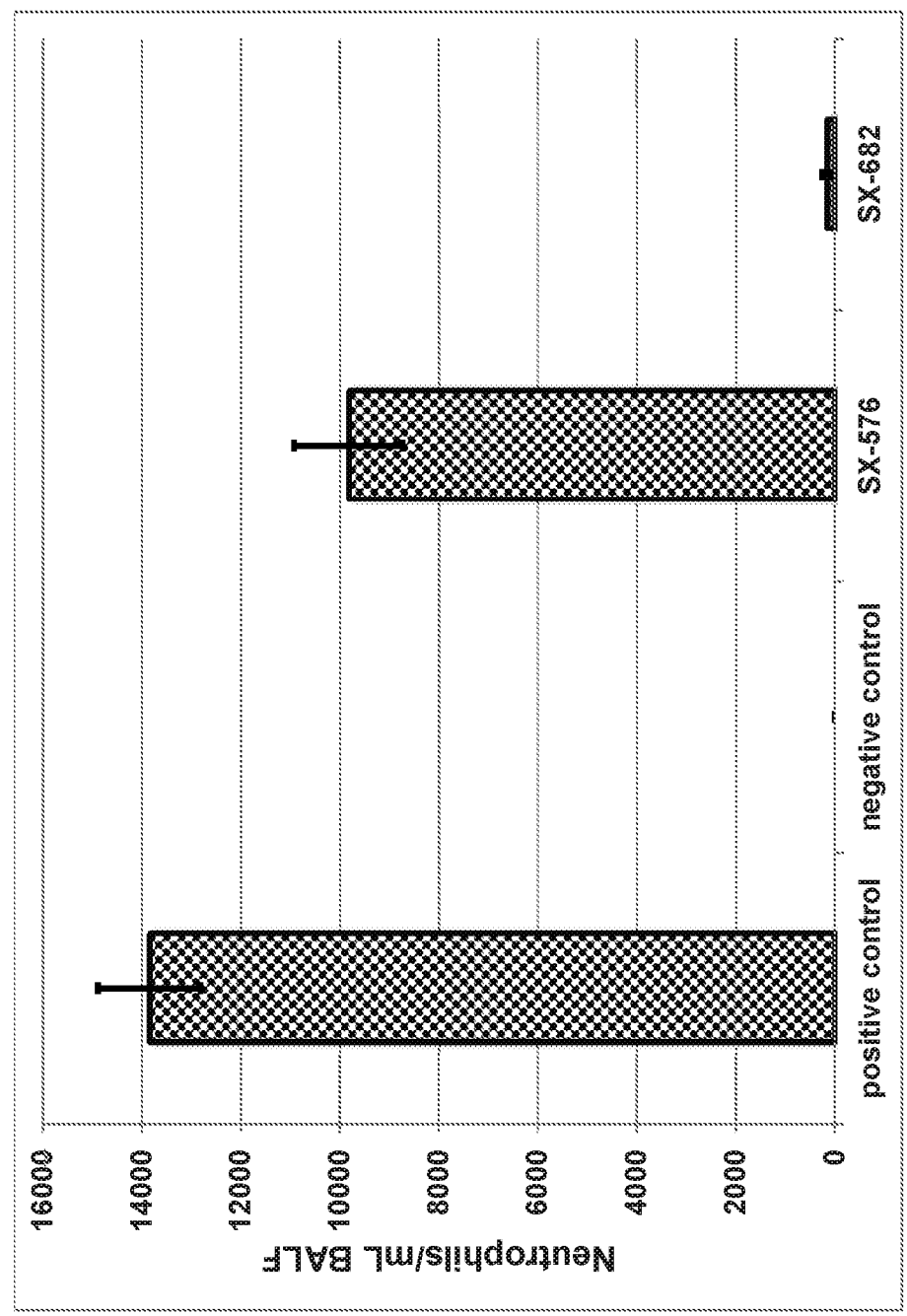
FIG. 4 shows the effect of intravenous dosing of either SX-576 or SX-682 on neutrophil influx in the ozone rat model of pulmonary inflammation.

SX-682 was assayed in an in vivo rat model of pulmonary inflammation. Activity in this model of pulmonary inflammation provides evidence that supports the use of SX-682 in the treatment of a number of pulmonary inflammatory diseases, including chronic obstructive pulmonary disease (COPD) and bronchopulmonary dysplasia (BPD). In this experiment, Sprague-Dawley rats (n=4 per cohort) were dosed intravenously only once at t=0 with either vehicle control (dimethylformamide/PEG400/saline, 40:40:20), positive inhibitor control (SX-576, 1 mg/kg) or the test compound (SX-682, 1 mg/kg). The rats were then placed in air (negative exposure group; vehicle control only) or 1 ppm ozone (positive exposure group; vehicle control, positive inhibitor control SX-576, and test compound SX-682) for 4 hours. The rats were then sacrificed at t=24 hours, and the bronchoalveolar lavage fluid (BALF) was collected. The cells were spun down, stained with Wright-Giemsa and counted. In the negative exposure group, no neutrophils were observed when stained. In the ozone exposed rats treated with vehicle however, there was a brisk influx of neutrophils of approximately 14,000 per mL of BALF (FIG. 4). In contrast, both SX-576 and SX-682 (each at 1 mg/kg) significantly decreased the influx of neutrophils into the lungs as compared to control rats treated with vehicle only (FIG. 4). Of the two inhibitors tested, SX-682 exhibited a markedly more robust inhibition of neutrophil chemotaxis (FIG. 4). Notably, the inhibition of neutrophil influx into the BALF was sustained for 24 hours after only a single dose of 1 mg/kg of SX-682. These results provide evidence that SX-682 is a potent inhibitor of pulmonary neutrophil chemotaxis in vivo, and is effective for treating diseases with a heightened pulmonary inflammation component, like COPD in a predictive in vivo model.

Metabolic Stability Example 1

Increased Microsomal Stability of SX-682

Figure 5:
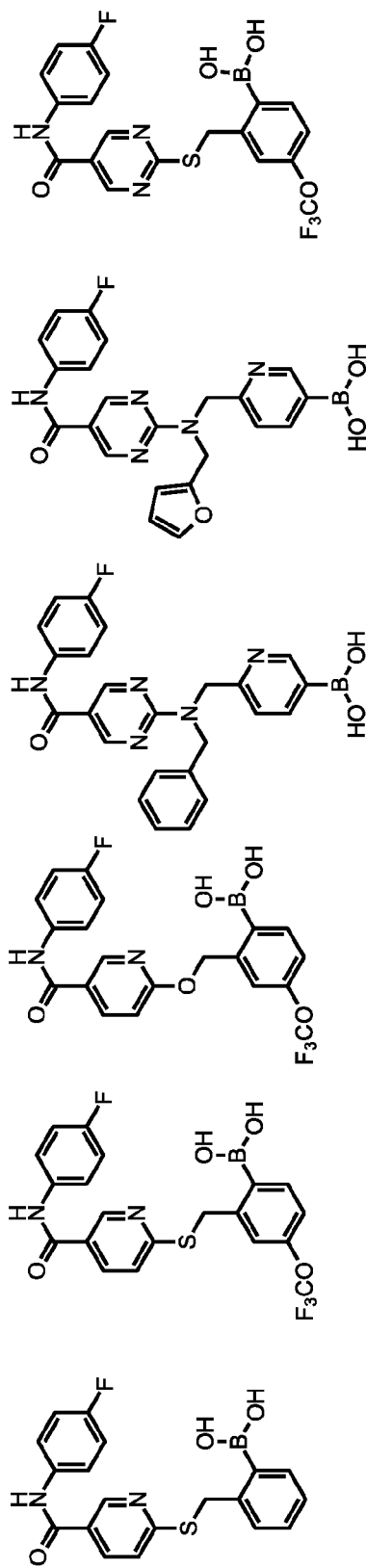
FIG. 5 illustrates boronic acid containing CXCR1/CXCR2 inhibitors.

Liver microsomes are an in vitro model for in vivo metabolism and elimination of a drug by the liver (and gut) cytochrome P450 system. A compound's stability in liver microsomes in vitro is predictive of its metabolism and elimination in vivo. We examined the stability of SX-682 in liver microsomes together with several other cogeners to quantify the microsomal stability of SX-682 and identify potential structure-activity relationships (SAR) predictive of stability or instability (FIG. 5).

The compounds were incubated in duplicate with human liver microsomes at 37° C. The reaction contained microsomal protein in 100 mM potassium phosphate, 2 mM NADPH, 3 mM $MgCl_2$, pH 7.4. A control was run for each compound omitting NADPH to detect NADPH-independent degradation. An aliquot was removed from each experimental and control reaction at 0, 10, 20, 30, and 60 minutes and mixed with an equal volume of ice-cold Stop Solution (0.3% acetic acid in acetonitrile containing haloperidol, diclofenac, or other internal standard). Stopped reactions were incubated for at least ten minutes at −20° C., and an additional volume of water was added. The samples were centrifuged to remove precipitated protein, and the supernatants were analyzed by LCMS/MS to quantitate the remaining compound. Data were converted to percent remaining by dividing by the time zero concentration value. Data were fit to a first-order decay model to determine half-life. Intrinsic clearance was calculated from the half-life and the protein concentrations:

$CL_{int} = \ln(2)/(t\frac{1}{2}[\text{microsomal protein}])$.

The results are shown in Table 1. Surprisingly, SX-682 was markedly more stable than SX-671 or SX-576 (6-fold larger half-life), even though the latter is structurally identical but for a single ring nitrogen. On the other hand, the introduction of a ring nitrogen was insufficient alone to impart the stability seen with SX-682 as demonstrated by SX-677 and SX-678, which have half-lives that are 2-fold and 5-fold smaller than SX-682, respectively. More surprising is that eliminating the ring nitrogen in SX-517 yielded a half-life even larger than that of SX-682. The results as a whole led to no SAR predictive of the surprising stability of SX-682.\

TABLE 1

Stability in human liver microsomes (NADPH-dependent)

| Parameter | SX-517 | SX576 | SX-671 | SX-677 | SX-678 | SX-682 |
|---|---|---|---|---|---|---|
| $CL_{int}{}^a$ (µL/min mg) | 3.4 | 45.7 | 16.2 | 15.9 | 33.4 | 2.1 |
| $t\frac{1}{2}{}^b$ (min) | 405 | 50 | 143 | 145 | 69.2 | 325 |

$^a$microsomal intrinsic clearance
$^b$half-life

Metabolic Stability Example 2

Increased Plasma Stability of SX-682

The in vitro stability of SX-682 and the cogeners of Metabolic Stability Example 1 (FIG. 5) were further studied in human plasma. The reactions were initiated by the addition of 5 µL of a 500 µM DMSO stock solution to 495 µL of preheated plasma solution to yield a final concentration of 5 µM. The assays were performed in a heat block at 37° C. and conducted in duplicate. Samples (50 µL) were taken at 0, 30, 60, 120, 240 min and added to 150 µL acetonitrile in order to deproteinize the plasma. The samples were subjected to vortex mixing for 1 min and then centrifugation for 15 min at 14,000 rpm. The clear supernatants were analyzed by LC-MS.

The in vitro plasma half-life (t½) was calculated using the expression $t\frac{1}{2} = \ln(2)/b$ where b is the slope found in the linear fit of the natural logarithm of the fraction remaining of the parent compound vs. incubation time.

The results are shown in Table 2. In the case of plasma stability, SX-682 is roughly as stable as SX-576 in contradistinction to its markedly enhanced stability in liver microsomes. Apparently, eliminating the ring nitrogen has little impact on plasma stability. On the other hand, also changing the sulfur to oxygen in SX-671 resulted in a pronounced 35-fold reduction in plasma half-life. However, keeping the sulfur is insufficient alone to maintain plasma stability as illustrated by SX-517, which maintains the sulfur but eliminates the ring $F_3CO$ group and results in a 5-fold reduction in plasma half-life.

TABLE 2

Stability in human plasma (incubation at 37° C., LC-MS/MS detection)

| Parameter | SX-517 | SX-576 | SX-671 | SX-677 | SX-678 | SX-682 |
|---|---|---|---|---|---|---|
| t½ (min) | 113 | 533 | 21 | 2310 | 3465 | 693 |

What is claimed:

1. A method for treating a subject with a cancer, comprising administering to the subject in need thereof a therapeutically effective amount of the compound having formula SX-682

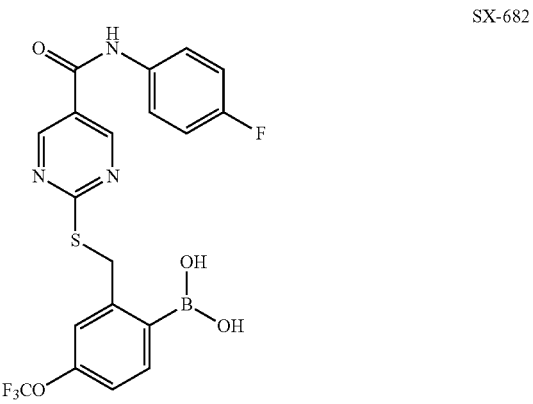 [SMILES: O=C(Nc1ccc(F)cc1)c1cnc(SCc2cc(OC(F)(F)F)ccc2B(O)O)nc1]

SX-682 or a pharmaceutically acceptable salt or solvate thereof.

2. The method of claim 1, wherein SX-682 or a pharmaceutically acceptable salt or solvate thereof is administered concurrently or sequentially with at least one antineoplastic agent.

3. The method of claim 2, wherein the antineoplastic agent is selected from nitrogen mustards, ethylenimine derivatives, alkyl sulfonates, nitrosoureas and triazenes, uracil mustard, chlormethine, cyclophosphamide, ifosfamide, melphalan, chlorambucil, pipobroman, triethylenemelamine, triethylenethiophos-phoramine, busulfan, carmustine, lomustine, streptozocin, dacarbazine, and temozolomide.

4. The method of claim 2, wherein the antineoplastic agent is selected from folic acid antagonists, pyrimidine analogs, purine analogs and adenosine deaminase inhibitors, methotrexate, aminopterin, 5-fluorouracil, floxuridine, cytarabine, 6-mercaptopurine, 6-thioguanine, fludarabine phosphate, pentostatine, and gemcitabine.

5. The method of claim 2, wherein the antineoplastic agent is selected from vinca alkaloids, antitumor antibiotics, enzymes, lymphokines and epipodophyllotoxins, vinblastine, vincristine, vindesine, bleomycin, dactinomycin, daunorubicin, doxorubicin, epirubicin, idarubicin, paclitaxel (TAXOL®), mithramycin, deoxycoformycin, mitomycin-C, L-asparaginase, interferons (especially IFN-γ), etoposide, and teniposide.

6. The method of claim 2, wherein the antineoplastic agent is selected from 17α-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, and zoladex.

7. The method of claim 2, wherein the antineoplastic agent is selected from platinum coordination complexes, cisplatin, carboplatin, hydroxyurea, amsacrine, procarbazine, mitotane, mitoxantrone, levamisole, and hexamethylmelamine.

8. The method of claim 2, wherein the antineoplastic agent is selected from gemcitabine, paclitaxel, cyclophosphamide, 5-fluorouracil, temozolomide and vincristine.

9. The method of claim 1, wherein SX-682 or a pharmaceutically acceptable salt or solvate thereof, is administered concurrently or sequentially with a microtubule affecting agent selected from allocolchicine, halichondrin B, colchicine, colchicine derivatives, dolastatin 10, maytansine, rhizoxin, paclitaxel, TAXOL® derivatives, thiocolchicine, trityl cysteine, vinblastine sulfate, vincristine sulfate, epothilone A, epothilone, and discodermolide, estramustine, nocodazole, and MAP4.

10. The method of claim 1, wherein SX-682 or a pharmaceutically acceptable salt or solvate thereof, is administered concurrently or sequentially with an anti-angiogenesis agent, a VEGF receptor kinase inhibitor, an antibodies against the VEGF receptor, interferon, or radiation.

11. The method of claim 1, wherein the compound having formula SX-682 or a pharmaceutically acceptable salt or solvate thereof is administered orally, transdermally, parenterally, intranasally, or by inhalation.

12. The method of claim 1, wherein the compound having formula SX-682 or a pharmaceutically acceptable salt or solvate thereof is administered orally.

13. The method of claim 1, wherein the compound having formula SX-682 or a pharmaceutically acceptable salt or solvate thereof is administered in a 0.01 mg to 1000 mg dose.

14. The method of claim 1, wherein the compound having formula SX-682 or a pharmaceutically acceptable salt or solvate thereof is administered orally in a daily, twice-weekly or once-weekly dose of 0.04 mg to 4000 mg, given in two to four divided doses or as a single dose.

15. The method of claim 14, wherein the dose of the compound having formula SX-682 or a pharmaceutically acceptable salt or solvate thereof is 10 mg to 600 mg, 1000 mg, or 2000 mg.

16. A method for treating a subject with a tumor, comprising administering to the subject in need thereof a therapeutically effective amount of the compound having formula SX-682

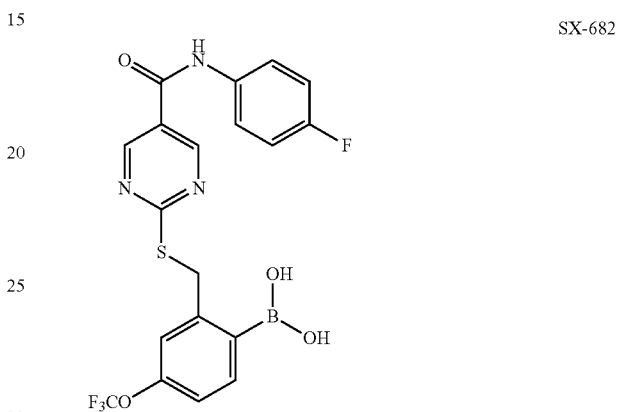

SX-682 or a pharmaceutically acceptable salt or solvate thereof.

17. The method of claim 16, further comprising the step of successively measuring the tumor.

18. The method of claim 17, wherein the tumor is measured by CAT or MRI scan.

19. The method of claim 17, wherein SX-682 inhibits angiogenesis associated with tumor growth.

20. The method of claim 17, wherein SX-682 inhibits growth of a tumor.

21. The method of claim 20, wherein SX-682 inhibits growth of systemic tumors, CNS tumors, tumors dependent on angiogenesis for growth.

22. The method of claim 17, wherein administration of SX-682 inhibits metastasis of a tumor.

23. The method of claim 17, wherein administration of SX-682 decreases the size of a tumor.

24. The method of claim 17, wherein administration of SX-682 decreases the volume of a tumor.

* * * * *